United States Patent
Darteil et al.

(10) Patent No.: US 12,104,209 B2
(45) Date of Patent: *Oct. 1, 2024

(54) NON-INVASIVE DIAGNOSTIC OF NON-ALCOHOLIC STEATOHEPATITIS

(71) Applicant: Genfit, Loos (FR)

(72) Inventors: Raphaël Darteil, Villeurbanne (FR); Geneviève Cordonnier, Templemars (FR); John Brozek, Saint-Amand-les-Eaux (FR); Emilie Praca, Lille (FR); Fouad Ben Sudrik, Lille (FR)

(73) Assignee: GENFIT, Loos (FR)

( * ) Notice: Subject to any disclaimer, the term of this patent is extended or adjusted under 35 U.S.C. 154(b) by 1640 days.

This patent is subject to a terminal disclaimer.

(21) Appl. No.: 16/089,835

(22) PCT Filed: Mar. 30, 2017

(86) PCT No.: PCT/EP2017/057633
§ 371 (c)(1),
(2) Date: Sep. 28, 2018

(87) PCT Pub. No.: WO2017/167934
PCT Pub. Date: Oct. 5, 2017

(65) Prior Publication Data
US 2019/0352715 A1   Nov. 21, 2019

(30) Foreign Application Priority Data
Mar. 30, 2016 (EP) .................................. 16163048

(51) Int. Cl.
| | | |
|---|---|---|
| C12Q 1/6883 | (2018.01) | |
| A61K 31/216 | (2006.01) | |
| C12Q 1/54 | (2006.01) | |
| C12Q 1/6827 | (2018.01) | |
| G06F 17/18 | (2006.01) | |
| G16B 5/20 | (2019.01) | |
| G16B 25/00 | (2019.01) | |
| G16B 40/10 | (2019.01) | |
| G16H 50/30 | (2018.01) | |

(52) U.S. Cl.
CPC .......... *C12Q 1/6883* (2013.01); *A61K 31/216* (2013.01); *C12Q 1/54* (2013.01); *C12Q 1/6827* (2013.01); *G06F 17/18* (2013.01); *G16B 5/20* (2019.02); *G16B 25/00* (2019.02); *G16B 40/10* (2019.02); *G16H 50/30* (2018.01); *C12Q 2600/106* (2013.01); *C12Q 2600/112* (2013.01); *C12Q 2600/118* (2013.01); *C12Q 2600/136* (2013.01); *C12Q 2600/158* (2013.01); *C12Q 2600/178* (2013.01); *G01N 2800/085* (2013.01)

(58) Field of Classification Search
CPC .......... G06F 17/18; G16B 5/20; G16B 25/00; G16B 40/10; G16H 50/30; C12Q 2600/158; C12Q 2600/178
See application file for complete search history.

(56) References Cited

U.S. PATENT DOCUMENTS

2012/0264824 A1   10/2012   Mizuguchi et al.

FOREIGN PATENT DOCUMENTS

| CN | 104293908 A | 1/2015 |
|---|---|---|
| WO | WO 2004/005243 A2 | 1/2004 |
| WO | 2006103570 A2 | 10/2006 |
| WO | WO 2012/105590 A1 | 8/2012 |
| WO | WO 2014/049131 A1 | 4/2014 |
| WO | WO 2015/192854 A2 | 12/2015 |
| WO | 2017046181 A1 | 3/2017 |

OTHER PUBLICATIONS

Cermelli S, Ruggieri A, Marrero JA, Ioannou GN, Beretta L, Circulating MicroRNAs in Patients with Chronic Hepatitis C and Non-Alcoholic Fatty Liver Disease 2011, PLOS ONE 6(8): e23937. https://doi.org/10.1371/journal (Year: 2011).*

Julia S Johansen, Per Christoffersen, Søren Møller, Paul A Price, Jens H Henriksen, Charly Garbarsch, Flemming Bendtsen, Serum YKL-40 is increased in patients with hepatic fibrosis 2001, Journal of Hepatology, vol. 32, Issue 6, (Year: 2001).*

Sanyal, Arun, et al.; "A New Method Including the Quantification of Circulating MIRNAs Allows the Efficient Identification of Nash Patients At Risk who Should Be Treated"; Retrived from the internet: http://www.genfit.com/wp=content/uploads/2016/05/Poster-GENFIT-Biomarkers-EASLILC16-SAT-431.pdg on May 29, 2017; Page.*

Obika, M., & Noguchi, H. (2012). Diagnosis and evaluation of nonalcoholic fatty liver disease. Experimental diabetes research, 2012, 145754. https://doi.org/10.1155/2012/145754 (Year: 2012).*

Clarke, John D., et al; "Circulating microRNA 122 in the Methionine and Choline Deficient Mouse Model of Nonalcoholic Steatohepatitis"; National Institutes of Health; J Appl Toxicol; Published Jun. 2014; pp. 726-732 Jun. 1, 2014.

Estep, M. et al.; "Differential expression of MiRNAs in the visceral adipose tissue of patients with non-alcoholic fatty liver disease"; Aliment Pharmacol Ther 2010; Blackwell Publishing Ltd; vol. 32, No. 3; Aug. 1, 2010; pp. 487-497 Aug. 1, 2010.

Sanyal, Arun, et al.; "A New Method Including the Quantification of Circulating MIRNAs Allows the Efficient Identification of Nash Patients At Risk who Should Be Treated"; Retrived from the Internet: http://www.genfit.com/wp-content/uploads/2016/05/Poster-GENFIT-Biomarkers-EASLILC16-SAT-431.pdg on May 29, 2017; pp. 1 Mar. 24, 2016.

(Continued)

*Primary Examiner* — Larry D Riggs, II
*Assistant Examiner* — Nidhi Dharithreesan
(74) *Attorney, Agent, or Firm* — SALIWANCHIK, LLOYD & EISENSCHENK

(57) ABSTRACT

The invention relates to a novel method for the diagnosis of non-alcoholic steatohepatitis (NASH), and for classifying a subject as a potential receiver of a treatment for NASH.

11 Claims, No Drawings
Specification includes a Sequence Listing.

(56) References Cited

OTHER PUBLICATIONS

Tryndyak, Volodymyr P., et al.; "Plasma microRNAs are sensitive indicators of inter-strain differences in the severity of liver injury induced in mice by a choline- and folate-deficient diet"; Toxicology and Applied Pharmacology; vol. 262, No. 1; Apr. 16, 2012; pp. 52-59 Apr. 16, 2012.
Anonymous; "Elafibranor—Wikipedia"; Retrieved from the Internet: https://en.wikipedia.org/wiki/Elafibranor on May 29, 2017; pp. 4 May 29, 2017.
Rui E. Castro, et al.; "miR-34a/SIRTI/p53 is suppressed by ursodeoxycholic acid in the rat liver and activated by disease severity in human non-alcoholic fatty liver disease"; EASL, Journal of Hepatology 2013 vol. 58 1119-125.
19th Euroconference on Apoptosis "Metabolism, Epigenetics and Death" and the 8th Training Course on "Concepts and Methods in Program Cell Death"; pp. 1-273; Sep. 14-17, 2011.
Onpan Cheung, et al.: "Nonalcoholic Steatohepatitis Is Associated with Altered Hepatic MicroRNA Expression"; HEPATOLOGY 2008; 48:1810-1820.
Duarte M. S. Ferreira, et al.; "Revisiting the metabolic syndrome and paving the way for microRNAs in non-alcoholic fatty liver disease" ; FEBS Journal 281 (2014) 2503-2524.
Balas et al., Different innate signatures induced in human monocyte-derived dendritic cells by wild-type dengue 3 virus, attenuated but reactogenic dengue 3 vaccine virus, or attenuated nonreactogenic dengue 1-4 vaccine virus strains. J Infect Dis. Jan. 1, 2011;203(1):103-8.
Blaney et al., Genetic basis of attenuation of dengue virus type 4 small plaque mutants with restricted replication in suckling mice and in SCID mice transplanted with human liver cells. Virology. Aug. 15, 2002;300(1):125-39.
Butrapet et al., Attenuation markers of a candidate dengue type 2 vaccine virus, strain 16681 (PDK-53), are defined by mutations in the 5' noncoding region and nonstructural proteins 1 and 3. J Virol. Apr. 2000;74(7):3011-9.
Cho et al., YKL-40 is a Protective Biomarker for Fatty Liver in World Trade Center Particulate Matter-Exposed Firefighters. J Mol Biomark Diagn. 2014;5:1000174(17 pages).
Faye et al., Quantitative real-time PCR detection of Zika virus and evaluation with field-caught mosquitoes. Virol J. Oct. 22, 2013;10:311.
Fisher, Evaluation of High-Throughput Methodology for Multi-Gene Screening in Patients with Non-Alcoholic Fatty Liver Disease (NAFLD). Thesis at Stellenbosch University. Dec. 2011. 202 pages.
Kamada et al., [Update on NAFLD diagnosis and test methods]. J Japanese Soc Gastroenterol. 2014;111:25-34.
Kinney et al., Construction of infectious cDNA clones for dengue 2 virus: strain 16681 and its attenuated vaccine derivative, strain PDK-53. Virology. Apr. 14, 1997;230(2):300-8.
Lauring et al., Rationalizing the development of live attenuated virus vaccines. Nat Biotechnol. Jun. 2010;28(6):573-9. Epub Jun. 7, 2010.
Neuschwander-Tetri, Non-alcoholic fatty liver disease. BMC Med. Feb. 28, 2017;15(1):45(6 pages).
Perez-Cidoncha et al., Generation of replication-proficient influenza virus NS1 point mutants with interferon-hyperinducer phenotype. PLoS One. Jun. 2, 2014;9(6):e98668. 10 pages.
Pogribny et al., Difference in expression of hepatic microRNAs miR-29c, miR-34a, miR-155, and miR-200b is associated with strain-specific susceptibility to dietary nonalcoholic steatohepatitis in mice. Lab Invest. Oct. 2010;90(10):1437-46. Epub Jun. 14, 2010.
Ratziu et al., Elafibranor, an Agonist of the Peroxisome Proliferator-Activated Receptor-α and -δ, Induces Resolution of Nonalcoholic Steatohepatitis Without Fibrosis Worsening. Gastroenterology. May 2016;150(5):1147-1159.e5. Epub Feb. 11, 2016. Erratum in: Gastroenterology. Jun. 2017;152(8):2084.
Shu et al., MicroRNAs in modulating non-alcoholic steatohepatitis. Int J Clin Exp Med. Mar. 30, 2016;9(3):5366-78.
Staels et al., Hepatoprotective effects of the dual peroxisome proliferator-activated receptor alpha/delta agonist, GFT505, in rodent models of nonalcoholic fatty liver disease/nonalcoholic steatohepatitis. Hepatology. Dec. 2013;58(6):1941-52. Epub Oct. 29, 2013.
Talon et al., Influenza A and B viruses expressing altered NS1 proteins: A vaccine approach. Proc Natl Acad Sci U S A. Apr. 11, 2000;97(8):4309-14.
Zhang et al., Serum levels of microRNAs can specifically predict liver injury of chronic hepatitis B. World J Gastroenterol. Oct. 7, 2012;18(37):5188-96.
Zust et al., Rational design of a live attenuated dengue vaccine: 2'-o-methyltransferase mutants are highly attenuated and immunogenic in mice and macaques. PLoS Pathog. 2013;9(8):e1003521. Epub Aug. 1, 2013. Erratum in: PLoS Pathog. 2013;9(9). 13 pages.

\* cited by examiner

SEQUENCE LISTING

```
<160> NUMBER OF SEQ ID NOS: 20

<210> SEQ ID NO 1
<211> LENGTH: 22
<212> TYPE: RNA
<213> ORGANISM: Caenorhabditis elegans

<400> SEQUENCE: 1
ucaccgggug uaaaucagcu ug                                        22

<210> SEQ ID NO 2
<211> LENGTH: 22
<212> TYPE: RNA
<213> ORGANISM: Homo sapiens

<400> SEQUENCE: 2
uggaguguga caaugguguu ug                                        22

<210> SEQ ID NO 3
<211> LENGTH: 22
<212> TYPE: RNA
<213> ORGANISM: Homo sapiens

<400> SEQUENCE: 3
uggcaguguc uuagcugguu gu                                        22

<210> SEQ ID NO 4
<211> LENGTH: 22
<212> TYPE: RNA
<213> ORGANISM: Homo sapiens

<400> SEQUENCE: 4
uaacacuguc ugguaacgau gu                                        22

<210> SEQ ID NO 5
<211> LENGTH: 23
<212> TYPE: RNA
<213> ORGANISM: Homo sapiens

<400> SEQUENCE: 5
uagcaccauu ugaaaucagu guu                                       23

<210> SEQ ID NO 6
<211> LENGTH: 21
<212> TYPE: RNA
<213> ORGANISM: Homo sapiens

<400> SEQUENCE: 6
cugaccuaug aauugacagc c                                         21

<210> SEQ ID NO 7
<211> LENGTH: 23
<212> TYPE: RNA
<213> ORGANISM: Homo sapiens

<400> SEQUENCE: 7
agcuacauug ucugcugggu uuc                                       23

<210> SEQ ID NO 8
<211> LENGTH: 23
<212> TYPE: RNA
<213> ORGANISM: Homo sapiens

<400> SEQUENCE: 8
```

-continued agcagcauug uacagggcua uga                                          23

<210> SEQ ID NO 9
<211> LENGTH: 23
<212> TYPE: RNA
<213> ORGANISM: Homo sapiens

<400> SEQUENCE: 9
uuaaugcuaa ucgugauagg ggu                                          23

<210> SEQ ID NO 10
<211> LENGTH: 23
<212> TYPE: RNA
<213> ORGANISM: Homo sapiens

<400> SEQUENCE: 10
cccaguguuc agacuaccug uuc                                          23

<210> SEQ ID NO 11
<211> LENGTH: 22
<212> TYPE: RNA
<213> ORGANISM: Caenorhabditis elegans
<220> FEATURE:
<221> NAME/KEY: misc_feature
<222> LOCATION: (1)..(1)
<223> OTHER INFORMATION: modified with 5'-phosphorylation

<400> SEQUENCE: 11
ucaccgggug uaaaucagcu ug                                           22

<210> SEQ ID NO 12
<211> LENGTH: 22
<212> TYPE: RNA
<213> ORGANISM: Homo sapiens
<220> FEATURE:
<221> NAME/KEY: misc_feature
<222> LOCATION: (1)..(1)
<223> OTHER INFORMATION: modified with 5'-phosphorylation

<400> SEQUENCE: 12
uggaguguga caauggiguu ug                                           22

<210> SEQ ID NO 13
<211> LENGTH: 23
<212> TYPE: RNA
<213> ORGANISM: Homo sapiens
<220> FEATURE:
<221> NAME/KEY: misc_feature
<222> LOCATION: (1)..(1)
<223> OTHER INFORMATION: modified with 5'-phosphorylation

<400> SEQUENCE: 13
uagcaccauu ugaaaucagu guu                                          23

<210> SEQ ID NO 14
<211> LENGTH: 22
<212> TYPE: RNA
<213> ORGANISM: Homo sapiens
<220> FEATURE:
<221> NAME/KEY: misc_feature
<222> LOCATION: (1)..(1)
<223> OTHER INFORMATION: modified with 5'-phosphorylation

<400> SEQUENCE: 14
uggcaguguc uuagcugguu gu                                           22

```
<210> SEQ ID NO 15
<211> LENGTH: 21
<212> TYPE: RNA
<213> ORGANISM: Homo sapiens
<220> FEATURE:
<221> NAME/KEY: misc_feature
<222> LOCATION: (1)..(1)
<223> OTHER INFORMATION: modified with 5'-phosphorylation

<400> SEQUENCE: 15
cugaccuaug aauugacagc c                                         21

<210> SEQ ID NO 16
<211> LENGTH: 23
<212> TYPE: RNA
<213> ORGANISM: Homo sapiens
<220> FEATURE:
<221> NAME/KEY: misc_feature
<222> LOCATION: (1)..(1)
<223> OTHER INFORMATION: modified with 5'-phosphorylation

<400> SEQUENCE: 16
agcuacauug ucugcugggu uuc                                       23

<210> SEQ ID NO 17
<211> LENGTH: 23
<212> TYPE: RNA
<213> ORGANISM: Homo sapiens
<220> FEATURE:
<221> NAME/KEY: misc_feature
<222> LOCATION: (1)..(1)
<223> OTHER INFORMATION: modified with 5'-phosphorylation

<400> SEQUENCE: 17
agcagcauug uacagggcua uga                                       23

<210> SEQ ID NO 18
<211> LENGTH: 23
<212> TYPE: RNA
<213> ORGANISM: Homo sapiens
<220> FEATURE:
<221> NAME/KEY: misc_feature
<222> LOCATION: (1)..(1)
<223> OTHER INFORMATION: modified with 5'-phosphorylation

<400> SEQUENCE: 18
uuaaugcuaa ucgugauagg ggu                                       23

<210> SEQ ID NO 19
<211> LENGTH: 23
<212> TYPE: RNA
<213> ORGANISM: Homo sapiens
<220> FEATURE:
<221> NAME/KEY: misc_feature
<222> LOCATION: (1)..(1)
<223> OTHER INFORMATION: modified with 5'-phosphorylation

<400> SEQUENCE: 19
cccaguguuc agacuaccug uuc                                       23

<210> SEQ ID NO 20
<211> LENGTH: 22
<212> TYPE: RNA
<213> ORGANISM: Homo sapiens
<220> FEATURE:
<221> NAME/KEY: misc_feature
<222> LOCATION: (1)..(1)
<223> OTHER INFORMATION: modified with 5'-phosphorylation
```

```
<400> SEQUENCE: 20
uaacacuguc ugguaacgau gu                                          22
```

NON-INVASIVE DIAGNOSTIC OF NON-ALCOHOLIC STEATOHEPATITIS

CROSS-REFERENCE TO RELATED APPLICATIONS

This application is a national stage filing under 35 U.S.C. 371 of International Patent Application Serial Number PCT/EP2017/057633, filed Mar. 30, 2017, which claims the benefit of priority to European Patent Application No. 1163048.8, filed Mar. 30, 2016, the entire contents of each of which are incorporated by reference herein.

SEQUENCE LISTING

The instant application contains a Sequence Listing which has been filed electronically in ASCII format and is hereby incorporated by reference in its entirety. Said ASCII copy, created on Sep. 28, 2018, is named A101570016US00-SEQ-YJC.txt and is 3,273 bytes in size.

FIELD OF THE INVENTION

The invention relates to a novel method for the diagnosis of non-alcoholic steatohepatitis (NASH), and for classifying a subject as a potential receiver of a treatment for NASH.

BACKGROUND OF THE INVENTION

Non-alcoholic fatty liver disease (NAFLD) is a progressive liver disease that ranges from simple steatosis to non-alcoholic steatohepatitis (NASH).

Non-alcoholic steatohepatitis (NASH) is also a progressive disease of the liver characterized histologically by fatty acid accumulation, hepatocyte damage and inflammation resembling alcoholic hepatitis. NASH is a critical stage in the process that can lead to cirrhosis, liver failure and/or HCC (Hepatocellular Carninoma). A careful history of a lack of significant alcohol intake is essential to establish this diagnostic. NASH is one of the most common causes of elevated aminotransferases in patients referred for evaluation to hepatologists. Obesity and type-2 diabetes are associated to NASH.

Along with the obesity rates in the world, the incidence of NASH has increased in recent years, and patients who develop NASH have an increased rate of liver-related mortalities. Since the prevalence of these diseases is increasing, the prevalence of NASH is also expected to increase and therefore, this disease is becoming an emerging public issue in the United States as well as in other countries. Thus the growing prevalence and increased mortality associated with these diseases have underscored the need for i) greater mechanistic understanding of disease progression and ii) development of more sensitive and reliable method for a non-invasive diagnostic of NASH.

Because these diseases can be potentially reversed if diagnosed early enough, or at least their consequences limited, it seems to be crucial to be able to provide the medical field with new tools allowing such an early, rapid and precise diagnostic.

Although several attempts have been made to propose non-invasive methods for diagnosing and determining the activity, the stage, or the severity of NASH, as of today histological analysis of liver biopsies remains the optimal approach for differentiating NASH from early stage steatosis. Steatosis, lobular and portal inflammation, hepatocyte injury in the forms of ballooning and apoptosis, and fibrosis are features of NASH evaluated from the biopsy. However, liver biopsy has a number of obvious drawbacks. First, the material collected in liver biopsy represents only a very small part of the liver of the diagnosed subject, thereby raising doubts on whether the collected sample is representative of the global state of the subject's organ. Moreover, liver biopsy is a very invasive procedure that may be cumbersome, worrisome and painful for the patient, and which raises concerns about morbidity and mortality. At last, in view of the foregoing, liver biopsy cannot be reasonably proposed as a routine procedure for determining whether a person in the general population, or even patients at risk of NASH, suffers from NASH and/or for determining the activity, the stage, or the severity of NASH in said person.

Ultrasonography was also used to diagnose liver steatosis. However, this method is subjective as it is based on echo intensity (echogenicity) and special patterns of echoes (texture). As a result, it is not sensitive enough and often inaccurate, especially in patients with advanced fibrosis.

Current guidelines for the diagnosis of NASH recommend to use the AST/ALT ratio in non-severe patients (Angulo P. N. Engl. J. Med. 2002 Apr. 18; 346(16):1221-31; Maher J J. Semin Gastrointest Dis. 2002; 13:31-9) and the liver biopsy in severe patients with the Maddrey discriminant function above 32 (Levitsky J, Mailliard M E. Semin Liver Dis. 2004; 24:233-47; Mathurin P, et al. Gastroenterology. 1996; 110: 1847-53; Mathurin P, et al. J Hepatol. 2002; 36:480-7).

As liver biopsy is still an invasive and costly procedure, with a potential sampling error, it could be advantageous to have a fast and easy method to perform test that would give a good predictive value of the level NASH in the patient.

Several studies have observed that some serum biomarkers of fibrosis had better diagnostic values than the standard serum markers as transaminases or ActiTest (Naveau S, et al., Clin Gastroenterol Hepatol. 2005; 3(2); Castera L, et al., J. Hepatol. 2000; 32:412-8; Annoni G, et al. Hepatology. 1989; 9:693-7; Nojgaard C, et al. J Hepatol. 2003; 39: 179-86; Chossegros P. 1995; 22 (2 Su[ppl): 96-9), but none of these studies has really identified an accurate combination of markers of NASH.

Moreover, in recent years, some trials were done to develop the use of non-invasive biomarkers which has gained importance in the field of hepatic diagnosis. For example, EP1846862B describes a non-invasive in vitro method for diagnostic alcoholic or non-alcoholic steatohepatitis from a serum or plasma sample of a patient and comprising the steps of measuring the concentration of 7 biochemical markers and then combining them through a logistic function in order to obtain an end value.

In WO 2014/049131 a blood test for the non-invasive diagnosis of non-alcoholic steatohepatitis based on a measurement of at least one biomarker reflecting apoptosis, at least one biomarker reflecting anthropometry, at least one biomarker reflecting metabolic activity and optionally at least one biomarker reflecting liver status and a combination between said biomarkers in a mathematical function was disclosed.

Several studies were conducted that compared and combined non invasive biomarkers to assess hepatic fibrosis, but also to compare the accuracies of different algorithms incorporating those non invasive biomarkers. The difficulty is to select the effective and relevant biomarkers, eventually to combine them through an algorithm, to analyze the different results and optionally to define in a good way responsive patients.

However, no such precise diagnosis method for NASH is currently available.

Therefore a strong need exists in providing accurate, non-invasive means for diagnosing and determining the activity, the stage, or the severity of NASH in a subject.

SUMMARY OF THE INVENTION

The present invention is based on a very fine and complete analysis of a vast number of variables determined from more than 300 high quality samples obtained from NASH patients during a clinical trial conducted by the Applicant (study GFT505-212-7-NCT01694849), including histological data obtained from liver biopsies of the patients. This study led to the discovery of key circulating factors (or biomarkers) indicative of NASH and of its severity or stage or activity.

The present invention discloses a method for the diagnosis of non-alcoholic steatohepatitis (NASH) and/or for determining the activity, the stage, or the severity of NASH in a subject, and/or for the classification of a subject as a receiver or non receiver of a treatment for NASH, and/or for the evaluation of the efficacy of a medical treatment, and/or for the determination of the progression or the regression of the pathology in NASH patients, and/or for the classification of a patient as a potential responder or non responder to a medical treatment, and/or for the prediction of disease outcome for a patient, and/or for the identification of surrogate markers of clinical relevant outcomes, comprising the measure of the level of blood, serum or plasma circulating hsa-miR-34 or one of its collinear variable, and at least one other blood, serum or plasma circulating marker of liver damage.

Other aspects and embodiments will be apparent from the following detailed description.

DETAILED DESCRIPTION OF THE INVENTION

The present invention is based on the quantification and/or the combination of particular circulating micro-RNA(s) (miRNA(s)) and other circulating biomarkers, such as biochemical biomarkers that are circulating markers of liver damage.

In particular, the Applicant has identified that among the miRNA disclosed in the art has potential markers of inflammation in the setting of NASH/NAFLD (hsa-miR-21, hsa-miR-24, hsa-miR-33a, hsa-miR-34a, hsa-miR-122 and hsa-miR-155), hsa-miR-34a is a key biomarker for diagnosing NASH.

Accordingly, a first aspect of the invention relates to a method for the diagnosis of NASH or for determining the activity, the stage, or the severity of NASH in a subject, comprising the measure of the level of blood, serum or plasma circulating hsa-miR-34a, and optionally at least one other blood, serum or plasma circulating marker of liver damage.

According to the invention, combinations of particular miRNA(s) and optionally of other particular biochemical markers can lead to a very accurate, non-invasive means for diagnosing and determining the activity, the stage, or the severity of NASH in a subject. Thus, the present invention discloses a combination of both types of markers in such a way that the method is very powerful and precise. The present method provides both selectivity and specificity with respect to NASH in a subject.

Thus, the present invention stems from the identification of a defined set of circulating markers that, when considered collectively, are indicative of NASH and/or of the activity, the stage, or the severity of NASH in the subject tested for NASH or for its severity or stage or activity. The invention relates in particular to a method for the diagnosis of non-alcoholic steatohepatitis (NASH) and/or for determining the activity, the stage, or the severity of NASH in a subject, combining the identification of circulating micro-RNA(s) (miRNA(s)) and other circulating markers of liver damage and the quantification of their level.

Recently, there has been a significant amount of enthusiasm surrounding circulating miRNA(s) as biomarkers for various diseases, including cancer, hepatitis, liver injury and NAFLD (nonalcoholic fatty liver disease) (Osman, Clin. Lab. 2012; 58:393-402; Cermelli et al., PloS. One, 2011; 6:e23937; Elfimova et al., Front Physiol. 2012; 3:476).

miRNA(s) are non-coding, small (from 19 to 25 nucleotides long), highly conserved regulatory RNAs, that regulate gene expression at the post-transcriptional level by partial repression or degradation of targeted mRNAs as an evolutionarily conserved molecular mechanism to modulate protein synthesis.

Currently, there are more than 2000 known miRNAs encoded in various intergenic, intronic or exonic sequences of human genome and it is estimated that miRNAs may directly target up to 60% of all human genes. miRNA(s) are involved in a wide array of biological processes, including cell apoptosis, differentiation, development, proliferation, and metabolism.

Circulating miRNA(s) are remarkably stable in the ribonuclease rich environment of the blood because they can be incorporated into ribonucleoprotein complexes or vesicles. miRNA(s) specific expression profiles are associated with several diseases, including some cancers, liver, heart, kidney and autoimmune disease. If the expression profiles of circulating miRNA(s) are strongly correlated with specific conditions, then the circulating miRNA(s) profile may act as a biomarker to diagnose and monitor diseases. miRNAs have recently emerged as novel biomarkers and potential therapeutic targets in the management of NAFLD.

Since their discovery miRNAs have been investigated for possible connections in human disease. Alterations in their expression patterns have been seen in multiple disease states compared to normal tissues and serum. In particular changes in miRNA expression in heart disease, sepsis, malignancies and autoimmune diseases have suggested a new avenue of research and targets for treating human diseases.

This promising new field has propelled research and opened the possibility that stable miRNAs which are detectable in serum and plasma may serve as biomarkers for early disease states or be non-invasive means of determining the severity of disease. However, miRNAs sufficiently potent and significantly indicative of a NASH, and methods implementing them were still needed, as the current gold standard for diagnosing or determining the stage of NASH is still liver biopsy.

Among the miRNA(s), hsa-miR-122 was proposed as a biomarker of liver disease (Chang et al., 2004; Lagos-Quintana et al., 2002).

Expression profiling studies have identified several differentially expressed miRNAs, including hsa-miR-21, hsa-miR-34a, hsa-miR-122, and hsa-miR-155 in human and mouse NASH, and that the altered expression of these miRNAs suggest a significant role in the pathogenesis of NASH. However, despite some recent success in the investigation and clinical management of NASH, major gaps remain. This includes limited understanding of the biochemical etiology, the broad spectrum of its presentation, and the basic process of disease progression from NAFLD to NASH.

In particular whether there is different susceptibility of certain patients or tissues to progress to NASH, and could this susceptibility be associated with an altered expression of miRNAs was still unknown.

As of today, no diagnosis test was available for the more precise diagnosis of NASH, based on an altered expression of miRNAs alone or in combination.

The present invention stems from the very fine analysis of the patients' biopsies during a clinical trial, to correlate the presence or level of circulating biological markers and to define different types of patients to be treated, according to the NAS scoring as described below. In particular the present invention non-limitatively defines three classes of NASH patients to be treated. These patients are classified with respect to the scoring of NASH characteristics.

In a particular embodiment, for each class of patients the Applicant defines a list of relevant biomarkers for several classes of patients. Further disclosed is a method which combines these different relevant biomarkers.

The different methods are thus directly in link with the patient to be treated. The methods according to the invention may allow classifying patients as being future receiver or non-receiver of a treatment of NASH, depending of their NASH score features. The patient to be treated may depend on regulatory agency or each country health policy. Here is provided a powerful tool for the physician to identify these patients to be treated, since the Applicant proposes different combinations of markers for identifying several classes of patients. Implementation of the methods of the invention results in the precise classification of the subjects under monitoring.

According to the invention, for each type of patient to be treated a NASH score may be obtained.

The present invention provides a method for classifying a subject as a receiver or non receiver, or as a potential receiver or potential non receiver, of a treatment for NASH. This classification may also be the base for further determining whether a subject should undergo further confirmation of NASH by methods known in the art such as by undergoing liver biopsy.

The method of the present invention may be used for
diagnosing NASH in a subject,
determining the activity of NASH in a subject,
determining the stage of NASH in a subject,
determining the severity of NASH in a subject,
classifying a subject as a receiver or non receiver of a treatment for NASH,
assessing the efficacy of a medical treatment of NASH, such as the efficacy of a drug,
determining the progression or regression of the pathology in a NASH patient,
determining the progression or regression of the pathology in a NASH patient after the administration of a medical treatment,
predicting if a patient will be receptive or not, i.e. (potentially) responder or (potentially) non responder to a medical treatment for NASH,
establishing a prognostic evaluation, i.e. a prediction of disease outcome,
providing surrogate markers of clinical relevant outcomes.

The methods of the invention allow diagnosing, but also following the evolution of NASH in a patient. These methods may advantageously be implemented for determining when to start a medical treatment for example, or to operate for the more critical patients (such as by liver transplantation).

The present invention is based on the fine combination of different biomarkers identified thanks to mathematical algorithms applied to the outcome of a large clinical study on the effect of Elafibranor, a very promising drug for the treatment of NASH. Elafibranor is GENFIT's lead pipeline product. Elafibranor is an oral once-daily treatment, and a first-in-class drug acting via dual peroxisome proliferator-activated alpha/delta pathways developed to treat, in particular, NASH. Elafibranor is believed to address multiple facets of NASH, including inflammation, insulin sensitivity, lipid/metabolic profile, and liver markers.

In a particular embodiment, different algorithms, each of them being dedicated to a specific class of patient are implemented.

By determining a specific algorithm according to the patient state, the further exploitation of the result is more fine and predictive.

Surprisingly, among all the miRNAs known to be somehow associated to NASH, hsa-miR-34 (or one of its collinear variables) has been determined by the present inventors as to be the most powerful and indicative biomarker of NASH, when combined with at least one other biomarker.

According to the present invention "non-alcoholic steatohepatitis" or "NASH" is defined as the presence of liver steatosis, hepatocyte ballooning and liver inflammation.

To this basic definition of the disease, NASH may further include liver fibrosis.

According to the present invention, the terms "subject" and "patient" are used interchangeably and designate a mammal subject, in particular a human subject or a human patient.

The invention, thanks to its non-invasive nature, may be implemented on any subject, such as a subject with no known or suspected predisposition to NASH.

However, in a particular embodiment, the subject is a subject at risk of having NASH or of developing NASH in the future, such as a subject having obesity, diabetes, suffering from the metabolic syndrome, or having elevated circulating level of liver enzymes (ALT and/or AST), or who was previously diagnosed with non-alcoholic fatty liver disease (or liver steatosis).

The subject may also be a subject with already identified NASH, the method of the invention thereby allowing determining the risks of evolution of the disease towards liver cirrhosis, fibrosis, hepatocarcinoma, liver transplantation or a cardiovascular disease.

When the subject is suffering from NASH, the method of the invention allows determining the efficacy of a drug for the treatment of the NASH disease, and also the classification as responder/non responder to the treatment of the patient.

The present invention may be implemented to identify patients that might be responder or non-responder to a treatment of NASH. In particular, the invention allows the classification of patients into different classes.

For each patient classification, a method is provided for the diagnosis of NASH, or for determining the activity, the stage, or the severity of NASH in a subject, or for the classification of a subject as a receiver or non-receiver of a treatment for non-alcoholic steatohepatitis (NASH), or for the assessment of the efficacy of a medical treatment of NASH, such as by administering a drug, or for the determination of the progression or the regression of the pathology in NASH patients; or for the determination of the progression or the regression of NASH after the administration of a medical treatment, or for the prediction if the patients will be receptive or not to a medical treatment, or for a prognostic evaluation, i.e. the prediction of disease outcome for a patient, or for the identification of surrogate markers of clinical relevant outcomes, and comprising the measure of the level of blood, serum or plasma of circulating hsa-miR-34 (e.g. hsa-miR-34a) or of its collinear variables, and of at least one other blood, serum or plasma circulating marker of liver damage.

The patient classification was defined according to histological features of liver biopsies from high quality samples of patients with NASH, during a clinical trial: hepatocellular steatosis, ballooning, lobular inflammation and, optionally, fibrosis.

Based on previous analysis, a NAFLD Activity Score (NAS) was established and can be defined as follow:

The NAS is based on 3 features, each of them being scored from 0 to 2 or 3, (see table below).

The NAS is the sum of the steatosis (S) score, the lobular inflammation (L) score and the hepatocyte ballooning (B) score.

The NAS can thus be comprised between 0 to 8.

Then, optionally, NASH patients may further be characterized by the stage of fibrosis, if any. The staging of fibrosis in NASH can be defined as 4 stages with three possibilities for stage 1, as shown below.

| NAS = total score: S + L + B (range 0-8) | | | | | |
|---|---|---|---|---|---|
| Steatosis | S score | Lobular inflammation | L score | Hepatocyte ballooning | B score |
| <5% | 0 | None | 0 | None | 0 |
| 5-33% | 1 | <2 foci/200X | 1 | Few ballooned cells | 1 |
| 34-66% | 2 | 2-4 foci/200x | 2 | Many ballooned cells | 2 |
| >66% | 3 | >4 foci/200x | 3 | | |
| Fibrosis | | | | Stage | |
| None | | | | 0 | |
| Mild, zone 3 perisinusoidal fibrosis | | | | 1a | |
| Moderate, zone 3 perisinusoidal fibrosis | | | | 1b | |
| Portal/periportal fibrosis only | | | | 1c | |
| Zone 3 perisinusoidal and portal/periportal fibrosis | | | | 2 | |
| Bridging fibrosis | | | | 3 | |
| Cirrhosis | | | | 4 | |

Source: Kleiner et al., Hepatology 2005; 41: 1313-21.

The data collected by the inventors were processed according to two different biostatistical approaches leading to the determination of a score that is indicative of the disease and/or its severity or stage or activity, thereby providing a powerful, accurate and highly predictive tool for the physician to easily determine whether a subject is suffering from NASH, or to determine the stage or activity or severity of the disease.

Two biostatistical approaches, the median model and the bootstrap model, were used to finely define combination of markers correlated to NASH patients, as described below.

The levels of the markers measured in the present invention are determined from a body fluid of the subject, which may in particular be a blood, more particularly a serum or a plasma sample. The sample may further correspond to another body fluid, such as urine.

According to a particular embodiment, the level of the markers, and especially of the miRNA(s), measured in the present invention are determined from a plasma sample, and preferably from a platelet-free plasma sample.

The level of the markers identified by the inventors may be determined by conventional methods well known in the art, such as immunoassays (e.g. ELISA), or molecular and biochemical assays (quantitative RT-PCR, colorimetric assays), or analytical methods (such as mass spectrometry), depending on the biomarker type (such as a protein, a micro-RNA, glucose level, . . . ).

When the tested marker is a micro-RNA, and more specifically hsa-miR-34a, its measure may be carried out according to a number of methods well-known in the art, such as that presented in the examples below.

Briefly, the measures are carried out from total RNA extracted from a blood, plasma or serum sample, in particular a cell-free, citrate-derived platelet-free plasma sample. An appropriate internal control (such as a micro-RNA of known sequence and quantity, e.g. *C. elegans* miR-39) may be added to the sample before RNA extraction. Cq values are determined using quantitative RT-PCR. Commercial kits are available for conducting such assays. For example, the Taqman miRNA qRT-PCR assay: Taqman MicroRNA Reverse transcription Kit, TaqMan MicroRNA Assay 20×, and TaqMan Universal Master Mix II (Applied Biosystems) may be used according to the manufacturer's instructions. Reverse transcription may be performed using readily available PCR systems, such as the GeneAmp® PCR System 9700 thermal cycler (Applied Biosystems), with appropriate cycling parameters such as 16° C. for 30 minutes followed by 42° C. for 30 minutes and 85° C. for 5 minutes before holding at 4° C. The reverse transcription may be implemented in the multiplexed format. Quantitative PCR is then conducted using a quantitative PCR system such as the CFX96TM Real-Time System (C1000 Touch™ Thermal Cycler, BioRad). Cycling conditions may be the following: 95° C. for 10 minutes followed by 95° C. for 15 sec and 60° C. for 60 sec for a total of 50 cycles and then 30° C. for 30 sec. Cq determination mode could be the Regression mode in the quantitative PCR system. In a particular embodiment, the Cq value determined according to the method of the invention is the Cq value which is obtainable using the above specific parameters and material. Cq values of samples may be excluded from the analysis if values are above the maximum Cq of the standard curve of each miRNA. The standard curve may be used to assess the reaction efficiency.

Serial dilution may be performed over eight points starting from the most concentrated cDNA sample, to ensure the standard curve covers all potential template concentrations that may be encountered during the study. The standard curve may be constructed by plotting the log of the starting quantity of the template against the Cq values obtained. To obtain absolute quantitative data synthetic hsa-miRNAs (e.g. from Integrated DNA Technologies) may be diluted at 3.125 fmol/mL and 5 μL may be used for reverse transcription concurrently with RNA extracted from serum samples. The product may then be serially diluted and PCR may be performed on all samples (standards and serum-derived RNA). Standard curve may be performed in duplicate and used to convert Cq data in copies/μL. The Cq Determination mode was Regression. Data used in the construction of the algorithm were in Log 10 (copies/μL of serum) format.

According to the present invention, a subject is diagnosed having NASH, or is diagnosed as potentially having NASH or likely to have NASH, when the level of hsa-miR-34a and the levels of at least one other marker, are increased, in particular when compared to reference values obtained from a control (or reference) sample. The reference sample may correspond to a body fluid sample, such as a blood, serum or plasma sample obtained from one or more subjects, such as two or more, who do not have NAFLD or NASH.

In the present invention, the levels of biomarkers, i.e. the level of hsa-miR-34 (e.g. hs-miR-34a), or of one of its collinear variables, and of at least one other marker, measured as described above may also be used to determine a disease score, otherwise named "NASH score". This score in the following description, is an invaluable and powerful tool for both the practitioner and the subjects in need thereof, as it allows the diagnosis of NASH, or the determination of the severity or stage or activity of NASH but also all parameters listed below, using a non-invasive procedure, i.e. without relying on liver biopsy. The NASH score may be compared with a threshold value that distinguishes between low, moderate, and high NASH activity, or moderate and severe NASH.

Moreover, the NASH score may also predict the efficacy of a medical treatment, such as a medical treatment based on a drug assimilation.

The NASH score provides surrogate markers of clinical relevant outcomes.

According to the present invention, this information may be advantageously used to determine whether a subject will receive or not a therapeutic treatment for NASH. According to a particular embodiment, a subject determined as a patient with NASH (either low, moderate or high NASH activity or severe NASH) will be treated with an appropriate NASH medical treatment. In a further particular embodiment, subjects with a moderate to high NASH activity or severe NASH will be treated.

Moreover, the calculation of the NASH score allows also to predict if a patient will be receptive or not to a medical treatment; i.e. responder or non-responder to a medical treatment.

In the same way, the NASH score permits to follow the progression or regression of the pathology in NASH patients. Additionally, it allows determining the progression or the regression of NASH after the administration of a medical treatment.

The NASH score also allows a prognostic evaluation, i.e. the prediction of disease outcome for a patient, such as his risk of developing cirrhosis.

Effectively, a high NASH score signifies that the patient is at risk and might evolve through a negative issue, i.e. cirrhosis or even death.

Accordingly, the present invention relates to a method for classifying a subject as a receiver or non receiver, or as a potential receiver or potential non receiver, of a treatment for NASH, said method comprising the determination of the levels of the markers as defined above, the calculation of a NASH score as provided herein, and the classification of the subject as (potential) receiver or (potential) non receiver of the treatment based on said NASH score. This classification may also be the base for further determining whether a subject should undergo further confirmation of NASH by methods known in the art such as by undergoing liver biopsy.

In addition, the classification of the subject may also be used to determine a low NASH activity or a moderate NASH in the subject, and providing to the subject based on this classification diet and/or lifestyle recommendations to reverse NASH.

The patient to be treated may have a low, moderate or high NASH activity, or present a severe NASH. However, according to a preferred embodiment, the Applicant starts from the premise that the patient to be treated is defined to be a patient at risk.

So the patient considered in the present invention is preferably classified as moderate to severe NASH patient.

According to a particular embodiment, the present invention, those subjects classified as moderate to high NASH activity, or as severe NASH patients are considered as receivers, or potential receivers, of a treatment for NASH.

In the context of the present invention, generally a NASH patient is defined as presenting the following liver biopsy-derived grades:
  steatosis score ≥1
  hepatocyte ballooning score ≥1
  lobular inflammation score ≥1
  NAS (NAFLD Activity Score)≥3 (NAS is defined as the sum of the steatosis score, hepatocyte ballooning score and lobular inflammation score).

The methods of the invention comprise the measure of hsa-miR-34 (e.g. hsa-miR-34a) or one of its collinear variables and at least one other blood, serum or plasma circulating marker of liver damage.

In a particular embodiment, the measurements of the levels of miRNA(s) are realized on plasma samples, and particularly on platelet-free plasma samples.

According to the statistical analysis, biomarkers were also tested through a collinearity test, as describe below.

When two or several variables present a correlation superior to 0.7, univariate test of difference in their mean in relation to the response variable defining patients were done. That means that the collinear variables are also included when they exist. The variable with best result in univariate test was selected among its collinear variables. These selected variables as well as other non-collinear variables are included in the modeling approach.

In the present invention, the levels of biomarkers measured as described above may also be used to determine a disease score, otherwise named "NASH score".

Thus, the present invention describes also a method wherein a NASH score is calculated from the measured levels of the blood, serum or plasma circulating markers of liver damage, and wherein NASH is diagnosed and/or NASH stage or activity or severity is determined and/or the classification of a subject as a receiver or non receiver of a treatment for NASH is determined and/or the efficacy of a medical treatment based on a drug administration is determined and/or the progression or the regression of the pathology in NASH patients is measured and/or of the progression or the regression of NASH after the administration of a medical treatment is measured and/or the character of a patient to be receptive or not to a medical treatment is determined and/or a prognostic evaluation, i.e. the prediction of disease outcome for a patient is established and/or a surrogate marker of clinical relevant outcomes is provided.

According to the invention, the method comprises the steps of:
  measuring the level of hsa-miR-34 or one of its collinear variable; and at least one blood, serum or plasma circulating marker of liver damage, and
  combining the results through a mathematical algorithm to obtain a NASH score.

In a particular embodiment, the at least one other circulating marker of liver damage is selected in the group consisting of alpha 2 macroglobulin, glycated haemoglobin (HbA1c), fasting glucose level, fructosamine level, insulin, C-Peptide, Homeostasis Model Assessment (HOMA), N-terminal pro-peptide of collagen type III, hsa-miR-200, YKL-40, CK18-M30, CK18-M65, ALT, AST, Uninary Specific Gravity (Uri Spec Grav), uninary creatinine, basophils, High Sensitivity-Reactive Protein (HSCRP), Urinary p-NAG, leucocytes, neutrophils and fibrinogen. These measure may be completed with other parameters, such as the measure of the height of the subject, as will be apparent below. In a particular embodiment, the method of the invention combines the measure of the level of miR34 (in particular hsa-miR-34a, more particularly hsa-miR-34a-5p) and the measure of the level of YKL-40. In a further particular embodiment, the method of the invention combines the measure of the level of miR34 (in particular hsa-miR-34a, more particularly hsa-miR-34a-5p) and the measure of the level of YKL-40 and alpha 2 macroglobulin. In another particular embodiment, the method of the invention combines the measure of the level of miR34 (in particular hsa-miR-34a, more particularly hsa-miR-34a-5p) and the measure of the level of YKL-40, alpha 2 macroglobulin and glycated haemoglobin (HbA1c).

According to the present invention, in the methods described herein, a change in the levels of the markers assayed relative to that of a control sample is indicative of NASH and/or of the activity, the stage, or the severity of NASH and/or of the classification of a subject as a receiver or non receiver of a treatment for NASH and/or of the efficacy of a medical treatment based on a drug administration and/or of the progression or the regression of the pathology in NASH patients and/or of the progression or the regression of NASH after the administration of a medical treatment and/or of the character of a patient to be receptive or not to a medical treatment, and/or of a prognostic evaluation, i.e. the prediction of disease outcome for a patient.

The NASH score, also referred to as "S", may refer in a particular embodiment to the probability of having a moderate to high NASH activity or a severe NASH.

First Subclass of Patients

In the context of the present invention and in a first variant of the invention, a first subclass of patient is defined as, or equivalent to, a patient presenting the following liver biopsy-derived grades:
  steatosis score ≥1
  hepatocyte ballooning score ≥1
  lobular inflammation score ≥1
  NAS (NAFLD Activity Score)≥4 (NAS is defined as the sum of the steatosis score, hepatocyte ballooning score and lobular inflammation score)
  fibrosis stage ≥2 (such as a fibrosis stage equal to 2, 3 or 4, in particular 2 or 3).

The following methods may be implemented to diagnose NASH in a subject, or to classify the subject as potentially presenting the above liver biopsy-derived grades, or to characterize the patient to be receiver or non-receiver of a treatment of NASH.

In a first variant of the method for identifying (or diagnosing) the first subclass of patients, hsa-miR-34 level is measured, in particular hsa-miR-34a, more particularly hsa-miR-34a-5p, and the collinear variable is selected in the group consisting of hsa-miR-122, in particular hsa-miR-122-5p, and hsa-miR-192, in particular hsa-miR-192-5p.

In a preferred embodiment of the first variant of the invention, the method comprises the steps of:
  measuring the level of hsa-miR-34, in particular hsa-miR-34a, more particularly hsa-miR-34a-5p; or hsa-miR-122, in particular hsa-miR-122-5p; or hsa-miR-192, in particular hsa-miR-192-5p; and
  measuring the level of at least one other marker, preferably all, selected in the group consisting of:
    alpha 2 macroglobulin,
    glycated haemoglobin (HbA1c), fasting glucose level or fructosamine level,
    N-terminal pro-peptide of collagen type III (PIIINP),
    hsa-miR-200, in particular hsa-miR-200a and more particularly hsa-miR-200a-3p),
    YKL-40.

In a particular embodiment of the first variant of the invention, the NASH score of the invention is calculated from the following marker levels measured as provided above:
  level of miR-34a (more particularly miR-34a-5p); and
  level of alpha 2 macroglobulin; and
  level of HbA1c; and
  level of N-terminal pro-peptide of collagen type III; and
  level of hsa-miR-200a, (in particular hsa-miR-200a-3p); and
  level of YKL-40.

In a further particular embodiment of the first variant, the score is defined as a logistic function:

$$S \sim \frac{e^Y}{1+e^Y}$$

wherein:

$$Y = k + a*A + b*B + c*C + d*D + f*F + g*G$$

wherein:
S is the NASH score according to the present invention;
A is the level of alpha 2 macroglobulin in g/L;
B is the level of HbA1c in percent (e.g. B is equal to 10 if measured HbA1c percentage is 10%);
C is the level of N-terminal pro-peptide of collagen type III in ng/mL;
D is the level of hsa-miR-34a (in particular hsa-miR-34a-5p) in Cq;
F is the level of hsa-miR-200 (in particular hsa-miR-200a, more particularly hsa-miR-200a-3p) in Cq;
G is the level of YKL-40 in pg/ml,
k is the constant of the logistic function;
a is a coefficient associated to the level of alpha 2 macroglobulin;
b is a coefficient associated to the level of HbA1c;
c is a coefficient associated to the level of N-terminal pro-peptide of collagen type III;
d is a coefficient associated to the level of hsa-miR-34a (in particular hsa-miR-34a-5p);
f is a coefficient associated to the level of hsa-miR-200 (in particular hsa-miR-200a, more particularly hsa-miR-200a-3p);
g is a coefficient associated to the level of YKL-40;

The NASH score thus is the probability of having a moderate to high NASH activity or a severe NASH.

If S is greater or equal to a threshold value, the subject is classified as having a NASH, or has having, or being potentially having a steatosis score ≥1, a hepatocyte ballooning score 1, a lobular inflammation score ≥1, a NAS ≥4 and a fibrosis stage ≥2 and/or is classified as to be treated for NASH, or to potentially be treated for NASH. According to a particular embodiment, if S is lower than a threshold value, the subject may be classified as to be treated or not to be treated, in particular not to be treated, and/or the subject is classified as receiver, or potential receiver, of diet and/or lifestyle advices for managing its low NASH activity or moderate NASH.

In a particular embodiment, derived from the median model as described in the experimental part of this application:
k is a number comprised between 5.94 and 50.74;
a is a number comprised between 0 and 1.07;
b is a number comprised between 0 and 1.20;
c is a number comprised between 0 and 0.24;
d is a number comprised between −0.97 and 0;
f is a number comprised between −0.87 and 0,
g is a number comprised between 0 and 1.74E-05;
and wherein the threshold value is comprised between 0.2017 and 0.4645, and is more particularly equal to 0.2302.

According to a particular embodiment, the subject is classified as having a NASH, or has having, or being potentially having a steatosis score ≥1, a hepatocyte ballooning score ≥1, a lobular inflammation score ≥1, a NAS ≥4 and a fibrosis stage ≥2 and/or is classified as a receiver, or potential receiver, of a treatment if the NASH score S is higher than or equal to a threshold value comprised between 0.2017 and 0.4645.

In a further particular embodiment, still derived from the median model:
k is equal to 25.13;
a is equal to 0.52;
b is equal to 0.57;
c is equal to 0.12;
d is equal to −0.43;
f is equal to −0.47; and
g is equal to 9,54E-06,
and wherein the threshold value is comprised between 0.2017 and 0.4645, and is more particularly equal to 0.2302.

According to a particular embodiment, the subject is classified as having a NASH, or has having, or being potentially having a steatosis score ≥1, a hepatocyte ballooning score ≥1, a lobular inflammation score ≥1, a NAS ≥4 and a fibrosis stage ≥2 and/or is classified as a receiver, or potential receiver, of a treatment if the NASH score S is higher than or equal to a threshold value comprised between 0.2017 and 0.4645.

According to this particular embodiment, the Area Under the Receiver Operating Characteristic (ROC) Curve (AUC) is at least equal to 0.80, and preferably 0.82, and more preferably 0.84. The AUC is a very well known criterion used in many applications to measure the quality of an algorithm. The more its value is close to 1, the better is the algorithm.

In another particular embodiment, derived from the bootstrap model as described in the experimental part of this application:
k is a number comprised between 8.24 and 35.44;
a is a number comprised between 0.06 and 0.88;
b is a number comprised between 0.14 and 1.04;
c is a number comprised between 0.03 and 0.23;
d is a number comprised between −0.75 and −0.05;
f is a number comprised between −0.73 and −0.07,
g is a number comprised between 3.59E-06 and 1.78E-05;
and wherein the threshold value is comprised between 0.2718 and 0.6391, and is more particularly equal to 0.3502.

According to a particular embodiment, the subject is classified as having a NASH, or has having, or being potentially having a steatosis score ≥1, a hepatocyte ballooning score ≥1, a lobular inflammation score ≥1, a NAS ≥4 and a fibrosis stage ≥2 and/or is classified as a receiver, or potential receiver, of a treatment if the NASH score S is higher than or equal to a threshold value comprised between 0.2718 and 0.6391.

In a further particular embodiment, also derived from the bootstrap model:
k is equal to 21.84;
a is equal to 0.47;
b is equal to 0.59;
c is equal to 0.13;
d is equal to −0.40;
f is equal to −0.40; and
g is equal to 1.07E-05
and wherein the threshold value is comprised between 0.2718 and 0.6391, and is more particularly equal to 0.3502.

According to a particular embodiment, the subject is classified as having a NASH, or has having, or being potentially having a steatosis score ≥1, a hepatocyte ballooning score ≥1, a lobular inflammation score ≥1, a NAS ≥4 and a fibrosis stage ≥2 and/or is classified as a receiver, or potential receiver, of a treatment if the NASH score S is higher than or equal to a threshold value comprised between 0.2718 and 0.6391.

According to this particular embodiment, the AUC is at least equal to 0.80, and preferably 0.82, and more preferably 0.84.

In a particular embodiment, the above methods described for the first variant are implemented from a plasma sample.

For both bootstrap and derived from the median models, the AUC are very good.

This mean that both model could be utilized interchangeability in the present invention.

The present invention also relates to a kit comprising means for determining the level of:
(i) at least one marker selected in the group consisting of hsa-miR-34 (in particular hsa-miR-34a, more particularly miR-34a-5p), hsa-miR-122 (in particular hsa-miR-122-5p) and hsa-miR-192 (in particular hsa-miR-192-5p); and at least one other, in particular all, marker selected in the group selected from:
(ii) alpha 2 macroglobulin;
(iii) at least one marker selected in the group consisting of HbA1c, fasting glucose level, fructosamine level;
(iv) N-terminal pro-peptide of collagen type III;
(v) hsa-miR-200 (in particular hsa-miR-200a, more particularly hsa-miR-200a-3p), and
(vi) YKL-40.

In a particular embodiment of the invention, said kit comprises means for determining the level of:
(i) hsa-miR-34 (in particular hsa-miR-34a, more particularly miR-34a-5p),
(ii) alpha 2 macroglobulin,
(iii) HbA1c,
(iv) N-terminal pro-peptide of collagen type III, and
(v) hsa-miR-200a (in particular hsa-miR-200a, more particularly hsa-miR-200a-3p) and YKL-40.

The kit of the invention is useful for implementing the methods described above may further optionally include instructions for implementing said methods. The kit may comprise reagents and buffers appropriate for conducting measures of the levels of markers identified above. In particular, the kit may comprise antibodies specific for a protein to be quantified, and/or primers useful for quantifying micro-RNA levels, as well-known in the art.

Among this first variant of the present invention, the Applicant went further in his researches and decided to focus on serum circulating miRNA(s).

Generally, the different circulating markers, and particularly the miRNA(s) are assessed from the plasma of the different patient at risk to be treated.

In a new approach, the Applicant assessed the different circulating markers on the sera. The serum can be defined as the clear yellowish fluid obtained upon separating whole blood into its solid and liquid components after it has been allowed to clot.

The miRNA(s) assessed from the sera are expressed in Log 10(copies/µl of serum) and a detailed method for determining this value is presented below.

In another model, the miRNA(s) assessed in the sera are expressed in Cq.

According to a preferred embodiment in which the miRNAs are assessed in the sera and expressed in Cq of the first variant of the invention, the method comprises the steps of:
measuring the serum level of hsa-miR-34, in particular hsa-miR-34a and more particularly hsa-miR-34a-5p, or hsa-miR-122 and in particular hsa-miR-122-5p, or CK18-M30, CK18-M65, or ALT or AST, and at least one blood, serum or plasma circulating marker of liver damage, and
combining the results through a mathematical algorithm to obtain a NASH score.

In another preferred embodiment of this aspect of the invention, the method comprises the steps of:
measuring the serum level of hsa-miR-34, in particular hsa-miR-34a and more particularly hsa-miR-34a-5p, or hsa-miR-122 and in particular hsa-miR-122-5p, or CK18-M30, CK18-M65, or ALT or AST,
measuring the level of alpha 2 macroglobulin,
measuring the level of glycated haemoglobin (HbA1c), fasting glucose level or fructosamine level,
measuring the level of YKL-40

In a particular embodiment of the first aspect of the invention, the NASH score of the invention is calculated from the following marker levels measured as provided above:
level of miR-34a (more particularly miR-34a-5p) measured in serum; and
level of alpha 2 macroglobulin in serum; and
level of YKL-40 in serum, and
level of HbA1c.

According to this particular embodiment, the score is defined as a logistic function with the serum level of has-miR-34a (in particular hsa-miR-34a-5p) expressed in Cq unit $$S \sim \frac{e^Y}{1+e^Y}$$

wherein:

$Y = k + a^*A + b^*B + c^*C + d^*D$ wherein:
S is the NASH score;
A is the serum level of hsa-miR-34a (in particular hsa-miR-34a-5p) in Cq;
B is the serum level of alpha 2 macroglobulin in g/L;
C is the serum level of YKL-40 in pg/ml,
D is the level of HbA1c in percent (e.g. D is equal to 10 if measured HbA1c percentage is 10%);
k is the constant of the logistic function
a is a coefficient associated to the serum level of hsa-miR-34a (in particular hsa-miR-34a-5p);
b is a coefficient associated to the serum level of alpha 2 macroglobulin;
c is a coefficient associated to the serum level of YKL-40;
d is a coefficient associated to the level of HbA1c.

If S is greater or equal to a threshold value, the subject is classified as having a NASH, or has having, or being potentially having a steatosis score ≥1, a hepatocyte ballooning score 1, a lobular inflammation score ≥1, a NAS ≥4 and a fibrosis stage ≥2 and/or is classified as to be treated for NASH, or to potentially be treated for NASH. According to a particular embodiment, if S is lower than a threshold value, the subject may be classified as to be treated or not to be treated, in particular not to be treated, and/or the subject is classified as receiver, or potential receiver, of diet and lifestyle advices for managing its low NASH activity or moderate NASH.

In a particular embodiment, derived from the bootstrap model as described in the experimental part of this application:
k is a number comprised between 9.51 and 34.37;
a is a number comprised between −1.17 and −0.47;
b is a number comprised between 0.02 and 0.84;
c is a number comprised between 6.10E-06 and 2.09E-05;
d is a number comprised between 0.07 and 0.89;
and wherein the threshold value is comprised between 0.2013 and 0.5965, and is more particularly equal to 0.4661.

According to a particular embodiment, the subject is classified as having a NASH, or has having, or being potentially having a steatosis score ≥1, a hepatocyte ballooning score ≥1, a lobular inflammation score ≥1, a NAS ≥4 and a fibrosis stage ≥2 and/or is classified as a receiver, or potential receiver, of a treatment if the NASH score S is higher than or equal to a threshold value comprised between 0.2013 and 0.5965.

In a further particular embodiment, also derived from the bootstrap model:
k is equal to 21.94;
a is equal to −0.82;
b is equal to 0.43;
c is equal to 1.35E-05;
d is equal to 0.48;
and wherein the threshold value is comprised between 0.2013 and 0.5965, and is more particularly equal to 0.4661.

According to a particular embodiment, the subject is classified as having a NASH, or has having, or being potentially having a steatosis score ≥1, a hepatocyte ballooning score ≥1, a lobular inflammation score ≥1, a NAS ≥4 and a fibrosis stage ≥2 and/or is classified as a receiver, or potential receiver, of a treatment if the NASH score S is higher than or equal to a threshold value comprised between 0.2013 and 0.5965.

According to this particular embodiment, the AUC is at least equal to 0.80, and preferably 0.82.

In a further particular embodiment, derived from the median model as described in the experimental part of this application:
k is a number comprised between 6.02 and 56.69;
a is a number comprised between −1.26 and 0.00;
b is a number comprised between 0.00 and 0.88,
c is a number comprised between 0.00 and 2.00E-05;
d is a number comprised between 0.00 and 0.96;
and wherein the threshold value is comprised between 0.9773 and 0.9955, and is more particularly equal to 0.9936.

According to a particular embodiment, the subject is classified as having a NASH, or has having, or being potentially having a steatosis 1, a hepatocyte ballooning score ≥1, a lobular inflammation score ≥1, a NAS ≥4 and a fibrosis stage ≥2 and/or is classified as a receiver, or potential receiver, of a treatment if the NASH score S is higher than or equal to a threshold value comprised between 0.9773 and 0.9955.

In a further particular embodiment, also derived from the median model:
k is equal to 28.17;
a is equal to −0.84;
b is equal to 0.36;
c is equal to 1.23E-05;
d is equal to 0.41;
and wherein the threshold value is comprised between 0.9773 and 0.9955, and is more particularly equal to 0.9936.

According to a particular embodiment, the subject is classified as having a NASH, or has having, or being potentially having a steatosis score ≥1, a hepatocyte ballooning score ≥1, a lobular inflammation score ≥1, a NAS ≥4 and a fibrosis stage ≥2 and/or is classified as a receiver, or potential receiver, of a treatment if the NASH score S is higher than or equal to a threshold value comprised between 0.9773 and 0.9955.

According to this particular embodiment, the AUC is at least equal to 0.80, and preferably 0.82.

For both bootstrap and derived from the median models, the AUC are very good.

This mean that both model could be utilized interchangeability in the present invention.

According also to a particular embodiment of the first variant of the invention, in which the miRNAs are assessed in the sera and expressed in copy/µl (log 10), the method comprises the steps of:
measuring the serum level of hsa-miR-34, in particular hsa-miR-34a and more particularly hsa-miR-34a-5p, or hsa-miR-122 and in particular hsa-miR-122-5p, or CK18-M30 or AST, and at least one blood, serum or plasma circulating marker of liver damage, and
combining the results through a mathematical algorithm to obtain a NASH score.

In another preferred embodiment of this first variant of the invention, the method comprises the steps of:
measuring the serum level of hsa-miR-34, in particular hsa-miR-34a and more particularly hsa-miR-34a-5p, or hsa-miR-122 and in particular hsa-miR-122-5p, or CK18-M30, or AST,
measuring the level of alpha 2 macroglobulin,
measuring the level of glycated haemoglobin (HbA1c), fasting glucose level or fructosamine level,
measuring the level of YKL-40.

According also to this particular embodiment, the score is defined as a logistic function with the serum level of has-miR-34a (in particular hsa-miR-34a-5p) expressed in copy/µl (log 10).

$$S \sim \frac{e^Y}{1+e^Y}$$

wherein:

$$Y = k + a*A + b*B + c*C + d*D$$

wherein:
S is the NASH score;
A is the serum level of hsa-miR-34a (in particular hsa-miR-34a-5p) in copy/pL (log 10);
B is the serum level of alpha 2 macroglobulin in g/L;
C is the serum level of YKL-40 in pg/ml,
D is the level of HbA1c in percent (e.g. D is equal to 10 if measured HbA1c percentage is 10%);
k is the constant of the logistic function
a is a coefficient associated to the serum level of hsa-miR-34a (in particular hsa-miR-34a-5p);
b is a coefficient associated to the serum level of alpha 2 macroglobulin;
c is a coefficient associated to the serum level of YKL-40;
d is a coefficient associated to the level of HbA1c.

The NASH score thus is the probability of having a moderate to high NASH activity or a severe NASH.

If S is greater or equal to a threshold value, the subject is classified as having a NASH, or has having, or being potentially having a steatosis score ≥1, a hepatocyte ballooning score 1, a lobular inflammation score ≥1, a NAS ≥4 and a fibrosis stage ≥2 and/or is classified as to be treated for NASH, or to potentially be treated for NASH. According to a particular embodiment, if S is lower than a threshold value, the subject may be classified as to be treated or not to be treated, in particular not to be treated, and/or the subject is classified as receiver, or potential receiver, of diet and/or lifestyle advices for managing its low NASH activity or moderate NASH.

In a particular embodiment, derived from the bootstrap model as described in the experimental part of this application:
k is a number comprised between −14.50 and −7.40;
a is a number comprised between 1.38 and 3.58;
b is a number comprised between 0.02 and 0.84.
c is a number comprised between 5.98E-06 and 2.08E-05;
d is a number comprised between 0.07 and 0.89;
and wherein the threshold value is comprised between 0.1895 and 0.6089, and is more particularly equal to 0.4255.

According to a particular embodiment, the subject is classified as having a NASH, or has having, or being potentially having a steatosis score ≥1, a hepatocyte ballooning score ≥1, a lobular inflammation score ≥1, a NAS ≥4 and a fibrosis stage ≥2 and/or is classified as a receiver, or potential receiver, of a treatment if the NASH score S is higher than or equal to a threshold value comprised between 0.1895 and 0.6089

In a further particular embodiment also derived from the bootstrap model:
k is equal to −10.95;
a is equal to 2.48;
b is equal to 0.43;
c is equal to 1.34E-05;
d is equal to 0.48;
and wherein the threshold value is comprised between 0.1895 and 0.6089, and is more particularly equal to 0.4255.

According to a particular embodiment, the subject is classified as having a NASH, or has having, or being potentially having a steatosis score ≥1, a hepatocyte ballooning score ≥1, a lobular inflammation score ≥1, a NAS ≥4 and a fibrosis stage ≥2 and/or is classified as a receiver, or potential receiver, of a treatment if the NASH score S is higher than or equal to a threshold value comprised between 0.1895 and 0.6089.

According to this particular embodiment, the AUC is at least equal to 0.80, and preferably 0.82.

In a further particular embodiment, derived from the median model as described in the experimental part of this application:
k is a number comprised between −27.16 and −0.78;
a is a number comprised between 0 and 3.97;
b is a number comprised between 0 and 0.89,
c is a number comprised between 0 and 1.98E-05;
d is a number comprised between 0 and 0.97;
and wherein the threshold value is comprised between 0.1421 and 0.4556, and is more particularly equal to 0.3201.

According to a particular embodiment, the subject is classified as having a NASH, or has having, or being potentially having a steatosis score ≥1, a hepatocyte ballooning score ≥1, a lobular inflammation score ≥1, a NAS ≥4 and a fibrosis stage ≥2 and/or is classified as a receiver, or potential receiver, of a treatment if the NASH score S is higher than or equal to a threshold value comprised between 0.1421 and 0.4556.

In a further particular embodiment:
k is equal to −11.03;
a is equal to 2.59;
b is equal to 0.38;
c is equal to 1.21E-05;
d is equal to 0.40;
and wherein the threshold value is comprised between 0.1421 and 0.4556, and is more particularly equal to 0.3201.

According to a particular embodiment, the subject is classified as having a NASH, or has having, or being potentially having a steatosis score ≥1, a hepatocyte ballooning score ≥1, a lobular inflammation score ≥1, a NAS ≥4 and a fibrosis stage ≥2 and/or is classified as a receiver, or potential receiver, of a treatment if the NASH score S is higher than or equal to a threshold value comprised between 0.1421 and 0.4556.

According to this particular embodiment, the AUC is at least equal to 0.80, and preferably 0.82.

In a last embodiment of this first variant concerning the miRNAs which are assessed in the sera and expressed in copy/µl (log 10), the Applicant also decided to transform the measured values of some of the other biomarkers into log 10 values. This means that the measured values of some markers defined above are expressed in log 0.

So according to this last embodiment of the first aspect of the invention, the method comprises the steps of:
measuring the serum level of hsa-miR-34, in particular hsa-miR-34a and more particularly hsa-miR-34a-5p, or hsa-miR-122 and in particular hsa-miR-122-5p, or CK18-M30, or ALT or AST, and at least one blood, serum or plasma circulating marker of liver damage, and
combining the results through a mathematical algorithm to obtain a NASH score In another preferred embodiment of this variant of the invention, the method comprises the steps of:
measuring the serum level of hsa-miR-34, in particular hsa-miR-34a and more particularly hsa-miR-34a-5p, or hsa-miR-122 and in particular hsa-miR-122-5p, or CK18-M30, or ALT or AST,
measuring the level of log 10(HOMA) (Homeostatis Model Assessment), or Fasting Glucose Plasma, or Fasting Glucose Serum, or log 10(Fructosamine), or HBA1C, or Insuline, or C-Peptide
measuring the level of log 10(YKL-40).

According also to this particular embodiment, the score is defined as a logistic function with the serum level of has-miR-34a (in particular hsa-miR-34a-5p) expressed in copy/µl (log 10).

$$S \sim \frac{e^Y}{1+e^Y}$$

wherein:

$Y=k+a*A+b*B+c*C$ wherein:
S is the NASH score;
A is the serum level of hsa-miR-34a (in particular hsa-miR-34a-5p) in copy/pL (log 10);
B is the serum level of log 10 (HOMA);
C is the serum level of log 10(YKL-40),
k is the constant of the logistic function
a is a coefficient associated to the serum level of hsa-miR-34a (in particular hsa-miR-34a-5p);
b is a coefficient associated to the serum level of log 10 (HOMA);
c is a coefficient associated to the serum level of log 10(YKL-40).

The NASH score thus is the probability of having a moderate to high NASH activity or a severe NASH.

If S is greater or equal to a threshold value, the subject is classified as having a NASH, or has having, or being potentially having a steatosis score ≥1, a hepatocyte ballooning score 1, a lobular inflammation score ≥1, a NAS ≥4 and a fibrosis stage ≥2 and/or is classified as to be treated for NASH, or to potentially be treated for NASH. According to a particular embodiment, if S is lower than a threshold value, the subject may be classified as to be treated or not to be treated, in particular not to be treated, and/or the subject is classified as receiver, or potential receiver, of diet and/or lifestyle advices for managing its low NASH activity or moderate NASH.

In a particular embodiment, derived from the bootstrap model as described in the experimental part of this application:
k is a number comprised between −25.68 and −13.34;
a is a number comprised between 1.62 and 3.78;
b is a number comprised between 0.40 and 2.52;
c is a number comprised between 1.37 and 3.61.

According to a particular embodiment, the subject is classified as having a NASH, or has having, or being potentially having a steatosis score ≥1, a hepatocyte ballooning score ≥1, a lobular inflammation score ≥1, a NAS ≥4 and a fibrosis stage ≥2 and/or is classified as a receiver, or potential receiver, of a treatment if the NASH score S is higher than or equal to a threshold value comprised between 0.2392 and 0.5907.

In a further particular embodiment still derived from the bootstrap model
k is equal to −19.51;
a is equal to 2.70;
b is equal to 1.46;
c is equal to 2.49;
and wherein the threshold value is comprised between 0.2392 and 0.5907, and is more particularly equal to 0.5313.

According to a particular embodiment, the subject is classified as having a NASH, or has having, or being potentially having a steatosis score ≥1, a hepatocyte ballooning score ≥1, a lobular inflammation score ≥1, a NAS ≥4 and a fibrosis stage ≥2 and/or is classified as a receiver, or potential receiver, of a treatment if the NASH score S is higher than or equal to a threshold value comprised between 0.2392 and 0.5907.

According to this particular embodiment, the AUC is at least equal to 0.80, and preferably 0.82.

Second Subclass of Patients

In the context of the present invention and in a second variant of the invention, a second subclass of patients is defined as, or equivalent to, a patient presenting the following liver biopsy-derived grades:

steatosis score ≥1
hepatocyte ballooning score ≥1
lobular inflammation score ≥1
NAS (NAFLD Activity Score) ≥4 (NAS is defined as the sum of the steatosis score, hepatocyte ballooning score and lobular inflammation score)
fibrosis stage ≥1 (such as a fibrosis stage equal to 1, 2, 3 or 4).

The methods of the invention comprise the measure of hsa-miR-34 or one of its collinear variable and at least one other blood, serum or plasma circulating marker of liver damage.

According to the statistical analysis, the biomarkers were also tested through a collinearity test, as describe below.

In a first variant of the method for identifying (or diagnosing) the second subclass of patients, hsa-miR-34 level is measured, in particular hsa-miR-34a, more particularly hsa-miR-34a-5p, and the collinear variable is selected in the group consisting of hsa-miR-122, in particular hsa-miR-122-5p, and hsa-miR-192, in particular hsa-miR-192-5p.

In a preferred embodiment of the second variant of the invention, the method comprises the steps of:

measuring the level of hsa-miR-34, in particular hsa-miR-34a, more particularly hsa-miR-34a-5p, and the collinear variable is selected in the group consisting of hsa-miR-122, in particular hsa-miR-122-5p, and hsa-miR-192, in particular hsa-miR-192-5p,
measuring the level of YKL-40; and optionally
measuring the level of Urinary Specific Gravity (Uri Spec Grav), or urinary creatinine;
measuring the level of basophils; and
measuring the level of HSCRP (High Sensitivity C-Reactive Protein).

In a more preferred embodiment of this second variant of the invention derived from the median model, the method comprises the steps of:

measuring the level of hsa-miR-34, in particular hsa-miR-34a and more particularly hsa-miR-34a-5p,
measuring the level of YKL-40.

In a particular embodiment of the second variant of the invention, the NASH score of the invention is calculated from the following marker levels measured as provided above:

level of miR-34a (more particularly miR-34a-5p); and
level of YKL-40.

In a further particular embodiment of the second variant of the invention, the score is defined as a logistic function:

$$S \sim \frac{e^Y}{1+e^Y}$$

wherein:

$$Y=k+a*A+b*B$$

wherein:
S is the NASH score;
A is the level of hsa-miR-34a (in particular hsa-miR-34a-5p) in Cq;
B is the level of YKL-40 in pg/ml;
k is a number comprised between −116.08 and 40.97;
a is a number comprised between −0.82 and 0;
b is a number comprised between 0 and 1.88E-05;
and wherein the threshold value is comprised between 0.1387 and 0.3481, and is more particularly equal to 0.2187.

According to a particular embodiment, the subject is classified as having a NASH, or has having, or being potentially having a steatosis score ≥1, a hepatocyte ballooning score ≥1, a lobular inflammation score ≥1, a NAS ≥4 and a fibrosis stage ≥1 and/or is classified as a receiver, or potential receiver, of a treatment if the NASH score S is higher than or equal to a threshold value comprised between 0.1387 and 0.3481, more particularly equal to 0.2187.

If S is greater or equal to a threshold value, the subject is classified as having a NASH, or has having, or being potentially having a steatosis score ≥1, a hepatocyte ballooning score 1, a lobular inflammation score ≥1, a NAS ≥4 and a fibrosis stage ≥1 and/or is classified as to be treated for NASH, or to potentially be treated for NASH. According to a particular embodiment, if S is lower than a threshold value, the subject may be classified as to be treated or not to be treated, in particular not to be treated, and/or the subject is classified as receiver, or potential receiver, of diet and/or lifestyle advices for managing its low NASH activity or moderate NASH.

In a particular embodiment, still derived from the median model as described in the experimental part of this application:

k is equal to 12,87;
a is equal to −0.42;
b is equal to 8.160E-06,
and wherein the threshold value is comprised between 0.1387 and 0.3481, and is more particularly equal to 0.2187.

According to a particular embodiment, the subject is classified as having a NASH, or has having, or being potentially having a steatosis score ≥1, a hepatocyte ballooning score ≥1, a lobular inflammation score ≥1, a NAS ≥4 and a fibrosis stage ≥1 and/or is classified as a receiver, or potential receiver, of a treatment if the NASH score S is higher than or equal to a threshold value comprised between 0.1387 and 0.3481, more particularly equal to 0.2187.

According to this particular embodiment, the AUC is at least equal to 0.68, and preferably 0.70.

In another preferred embodiment of this second variant of the invention derived from the bootstrap model, the method comprises the step of measuring the level of hsa-miR-34, in particular hsa-miR-34a and more particularly hsa-miR-34a-5p,
measuring the level of YKL-40,
measuring the level of urinary specific gravity,
measuring the level of basophils,
measuring the level of HSCRP,.

In a particular embodiment of the second variant of the invention, the NASH score of the invention is calculated from the following marker levels measured as provided above:

level of miR-34a (more particularly miR-34a-5p); and
level of YKL-40, and
level of urinary specific gravity, and
level of Basophils, and
level of HSCRP.

In a further particular embodiment of the second variant of the invention, the score is defined as a logistic function:

$$S \sim \frac{e^Y}{1+e^Y}$$

wherein:

$$Y = k + a*A + b*B + c*C + d*D + f*F$$

wherein:
S is the NASH score;
A is the level of hsa-miR-34a (in particular hsa-miR-34a-5p) in Cq;
B is the level of YKL-40 in pg/ml;
C is the level of urinary specific gravity (no units);
D is the level of basophils in 10e9/L;
F is the level of HSCRP in mg/dL
k is a number comprised between −124.81 and 1.13
a is a number comprised between −0.91 and −0.25;
b is a number comprised between 4.77e-06 and 2.39e-05;
c is a number comprised between 17.21 and 141.51;
d is a number comprised between 2.80 and 60.74;
f is a number comprised between 0.01 and 0.23;
and wherein the threshold value is comprised between 0.5791 and 0.8269 and is more particularly equal to 0.7758.

According to a particular embodiment, the subject is classified as having a NASH, or has having, or being potentially having a steatosis score ≥1, a hepatocyte ballooning score ≥1, a lobular inflammation score ≥1, a NAS ≥4 and a fibrosis stage ≥1 and/or is classified as a receiver, or potential receiver, of a treatment if the NASH score S is higher than or equal to a threshold value comprised between 0.5791 and 0.8269.

If S is greater or equal to a threshold value, the subject is classified as having, or as being potentially having a steatosis score ≥1, a hepatocyte ballooning score ≥1, a lobular inflammation score ≥1, a NAS ≥4 and a fibrosis stage ≥1 and/or is classified as to be treated for NASH, or to potentially be treated for NASH. According to a particular embodiment, if S is lower than a threshold value, the subject may be classified as to be treated or not to be treated, in particular not to be treated, and/or the subject is classified as receiver, or potential receiver, of diet and/or lifestyle advices for managing its low NASH activity or moderate NASH.

In a particular embodiment, derived from the bootstrap model as described in the experimental part of this application:
k is equal to −61.84;
a is equal to −0.58;
b is equal to 1.44E-05;
c is equal to 79.36;
d is equal to 31.77;
f is equal to 0.12,
and wherein the threshold value is comprised between 0.5791 and 0.8269 and is more particularly equal to 0.7758.

According to a particular embodiment, the subject is classified as having a NASH, or has having, or being potentially having a steatosis score ≥1, a hepatocyte ballooning score ≥1, a lobular inflammation score ≥1, a NAS ≥4 and a fibrosis stage ≥1 and/or is classified as a receiver, or potential receiver, of a treatment if the NASH score S is higher than or equal to a threshold value comprised between 0.5791 and 0.8269.

According to this particular embodiment, the AUC is at least equal to 0.75, and preferably 0.77.

The present invention also relates to a kit comprising means for determining the level of:
(i) at least one marker selected in the group consisting of hsa-miR-34 (in particular hsa-miR-34a, more particularly miR-34a-5p), or hsa-miR-122 and in particular hsa-miR-122-5p or hsa-miR-192 and in particular hsa-miR-192-5p, and
(ii) YKL-40; and optionally
(iii) Urinary Specific Gravity (Uri Spec Grav) or urinary creatinine; basophils; and HSCRP (High Sensitivity C-Reactive Protein), In a particular embodiment of the invention, said kit comprises means for determining the level of:
(i) hsa-miR-34 (in particular hsa-miR-34a, more particularly miR-34a-5p), and
(ii) YKL-40.

In another particular embodiment of the invention, said kit comprises means for determining the level of:
(i) hsa-miR-34 (in particular hsa-miR-34a, more particularly miR-34a-5p), and
(ii) YKL-40, and
(iii) Urinary Specific Gravity, and
(iv) basophils, and
(v) HSCRP.

The kit of the invention is useful for implementing the methods described above may further optionally include instructions for implementing said methods. The kit may comprise reagents and buffers appropriate for conducting measures of the levels of markers identified above. In particular, the kit may comprise antibodies specific for a protein to be quantified, and/or primers useful for quantifying micro-RNA levels, as well-known in the art.

Third Subclass of Patients

In the context of the present invention and in a third variant of the invention, a third subclass of patient is defined as, or equivalent to, a patient presenting the following liver biopsy-derived grades:
steatosis score ≥1
hepatocyte ballooning score ≥1
lobular inflammation score ≥1
NAS (NAFLD Activity Score) ≥4 (NAS is defined as the sum of the steatosis score, hepatocyte ballooning score and lobular inflammation score)
fibrosis stage=1b, 1c, 2, 3 or 4.

In a preferred embodiment of the third variant of the invention, the method comprises the steps of:
measuring the level of hsa-miR-34, in particular hsa-miR-34a and more particularly hsa-miR-34a-5a, or hsa-miR-122 and in particular hsa-miR-122-5p or hsa-miR-192 and in particular hsa-miR-192-5p,
measuring the level of CK18-M65, or CK18-M30, or AST or ALT and
measuring the level of Urinary p-NAG, and
measuring the level of Leukocytes, or Neutrophils, and
measuring the level of alpha 2 macroglobulin, and optionally
measuring the level of hsa-miR-200, in particular hsa-miR-200a and more particularly hsa-miR-200a-3p, and
measuring the level of fibrinogen, and
measuring the height of the patient.

In a more preferred embodiment of this third variant of the invention derived from the median model, the method comprises the steps of:
- measuring the level of hsa-miR-34, in particular hsa-miR-34a and more particularly hsa-miR-34a-5a, or hsa-miR-122 and in particular hsa-miR-122-5p or hsa-miR-192 and in particular hsa-miR-192-5p,
- measuring the level of CK18-M65, or CK18-M30, or AST or ALT and
- measuring the level of Urinary p-NAG, and
- measuring the level of Leukocytes, or Neutrophils, and
- measuring the level of alpha 2 macroglobulin,
- measuring the level of hsa-miR-200, in particular hsa-miR-200a and more particularly hsa-miR-200a-3p.

In a particular embodiment of the third aspect of the invention derived from the median model, the NASH score of the invention is calculated from the following marker levels measured as provided above:
- level of miR-34a (in particular miR-34a-5p), and
- level of CK18-M65, and
- level of Urinary p-NAG, and
- level of Leukocytes, and
- level of alpha 2 macroglobulin,
- level of hsa-miR-200a (in particular hsa-miR-200a-3p).

In a further particular embodiment of the third variant of the invention, the score is defined as a logistic function:

$$S \sim \frac{e^Y}{1+e^Y}$$

wherein:

$$Y = k + a^*A + b^*B + c^*C + d^*D + f^*F + g^*G$$

wherein:
S is the NASH score;
A is the level of in particular hsa-miR-34a (in particular hsa-miR-34a and more particularly hsa-miR-34a-5p) in Cq;
B is the level of CK18-M65 in U/L;
C is the level of Urinary p-NAG in U/L;
D is the level of Leukocytes in 10e9/L;
F is the level alpha 2 macroglobulin in g/L;
G is the level of has-miR-200a (in particular hsa-miR-200a-3p) in Cq,
k is a number comprised between −69.89 and 57.02;
a is a number comprised between −1.09 and 0;
b is a number comprised between 0 and 0.005;
c is a number comprised between 0 and 0.28;
d is a number comprised between 0 and 0.69;
f is a number comprised between 0 and 1.08;
g is a number comprised between −0.80 and 0;
and wherein the threshold value is comprised between 0.0197 and 0.1136, and is more particularly equal to 0.0592.

According to a particular embodiment, the subject is classified as having a NASH, or has having, or being potentially having a steatosis score ≥1, a hepatocyte ballooning score ≥1, a lobular inflammation score ≥1, a NAS ≥4 and a fibrosis stage=1b, 1c, 2, 3 or 4 and/or is classified as a receiver, or potential receiver, of a treatment if the NASH score S is higher than or equal to a threshold value comprised between 0.0197 and 0.1136, more particularly equal to 0.0592.

If S is greater or equal to a threshold value, the subject is classified as having a NASH, or has having, or being potentially having a steatosis score ≥1, a hepatocyte ballooning score 1, a lobular inflammation score ≥1, a NAS ≥4 and a fibrosis stage=1b, 1c, 2, 3 or 4 and/or is classified as to be treated for NASH, or to potentially be treated for NASH. According to a particular embodiment, if S is lower than a threshold value, the subject may be classified as to be treated or not to be treated, in particular not to be treated, and/or the subject is classified as receiver, or potential receiver, of diet and/or lifestyle advices for managing its low NASH activity or moderate NASH.

In a particular embodiment, still derived from the median model as described in the experimental part of this application:
k is equal to 24,98;
a is equal to −0.54;
b is equal to 0.002,
c is equal to 0.14,
d is equal to 0.32,
f is equal 0.43, and
g is equal to −0.37
and wherein the threshold value is comprised between 0.0197 and 0.1136, and is more particularly equal to 0.0592.

According to a particular embodiment, the subject is classified as having a NASH, or has having, or being potentially having a steatosis score ≥1, a hepatocyte ballooning score ≥1, a lobular inflammation score ≥1, a NAS ≥4 and a fibrosis stage=1b, 1c, 2, 3 or 4 and/or is classified as a receiver, or potential receiver, of a treatment if the NASH score S is higher than or equal to a threshold value comprised between 0.0197 and 0.1136, more particularly equal to 0.0592.

According to this particular embodiment, the AUC is at least equal to 0.80, and preferably 0.82, and more preferably 0.83.

In a more preferred embodiment of this third variant of the invention derived from the bootstrap model, the method comprises the steps of:
- measuring the level of hsa-miR-34, in particular hsa-miR-34a and more particularly hsa-miR-34a-5a, or hsa-miR-122 and in particular hsa-miR-122-5p or hsa-miR-192 and in particular hsa-miR-192-5p,
- measuring the level of CK18-M65, or CK18-M30, or AST or ALT and
- measuring the level of Urinary p-NAG, and
- measuring the level of Leukocytes, or Neutrophils, and
- measuring the level of alpha 2 macroglobulin, and
- measuring the level of Fibrinogen, and
- measuring the height.

In a particular embodiment of the third variant of the invention derived from the bootstrap model, the NASH score of the invention is calculated from the following marker levels measured as provided above:
- level of hsa-miR-34a, in particular hsa-miR-34a-5p,
- level of CK18-M65, and
- level of Urinary p-NAG, and
- level of Leukocytes, and
- level of alpha 2 macroglobulin,
- level of Fibrinogen,
- level of the height of the patient, In a further particular embodiment of the third variant of the invention, the score is defined as a logistic function:

$$S \sim \frac{e^Y}{1+e^Y}$$

wherein:

$$Y=k+a*A+b*B+c*C+d*D+f*F+g*G+h*H$$

wherein:
S is the NASH score;
A is the level of hsa-miR-34a (in particular hsa-miR-34a-5p) in Cq;
B is the level of CK18-M65 in U/L
C is the level of Urinary β-NAG in U/L
D is the level of Leukocytes in 10E9/L
F is the level alpha 2 macroglobulin in g/L
G is the level of fibrinogen in g/L,
H is the level of the height in cm,
k is a number comprised between 8.31 and 35.79;
a is a number comprised between −0.96 and −0.26;
b is a number comprised between 0.0006 and 0.0034;
c is a number comprised between 0.04 and 0.24;
d is a number comprised between 0.04 and 0.52;
f is a number comprised between 0.07 and 0.89;
g is a number comprised between 0.14 and 1.28;
h is a number comprised between −0.08 and −0.001;
and wherein the threshold value is comprised between 0.3373 and 0.7260, and is more particularly equal to 0.6370.

According to a particular embodiment, the subject is classified as having a NASH, or has having, or being potentially having a steatosis score ≥1, a hepatocyte ballooning score ≥1, a lobular inflammation score ≥1, a NAS ≥4 and a fibrosis stage=1b, 1c, 2, 3 or 4 and/or is classified as a receiver, or potential receiver, of a treatment if the NASH score S is higher than or equal to a threshold value comprised between 0.3373 and 0.7260, more particularly equal to 0.6370.

If S is greater or equal to a threshold value, the subject is classified as having a NASH, or has having, or being potentially having a steatosis score ≥1, a hepatocyte ballooning score 1, a lobular inflammation score ≥1, a NAS ≥4 and a fibrosis stage=1b, 1c, 2, 3 or 4 and/or is classified as to be treated for NASH, or to potentially be treated for NASH. According to a particular embodiment, if S is lower than a threshold value, the subject may be classified as to be treated or not to be treated, in particular not to be treated, and/or the subject is classified as receiver, or potential receiver, of diet and/or lifestyle advices for managing its low NASH activity or moderate NASH.

In a particular embodiment, still derived from the bootstrap model as described in the experimental part of this application:
k is equal to 22.05;
a is equal to −0.61;
b is equal to 0.002,
c is equal to 0.14,
d is equal to 0.28,
f is equal 0.48,
g is equal to 0.71, and
h is equal to −0.04
and wherein the threshold value is comprised between 0.3373 and 0.7260, and is more particularly equal to 0.6370.

According to a particular embodiment, the subject is classified as having a NASH, or has having, or being potentially having a steatosis score ≥1, a hepatocyte ballooning score ≥1, a lobular inflammation score ≥1, a NAS ≥4 and a fibrosis stage=1b, 1c, 2, 3 or 4 and/or is classified as a receiver, or potential receiver, of a treatment if the NASH score S is higher than or equal to a threshold value comprised between 0.3373 and 0.7260, more particularly equal to 0.6370.

According to this particular embodiment, the AUC is at least equal to 0.80, and preferably 0.82, and more preferably 0.84.

According to this third variant, the present invention also relates to a kit comprising means for determining the level of:
(i) at least one marker selected in the group of hsa-miR-34, (in particular hsa-miR-34a and more particularly hsa-miR-34a-5a), hsa-miR-122 and in particular hsa-miR-122-5p and hsa-miR-192 and in particular hsa-miR-192-5p, and
(ii) CK18-M65, or CK18-M30, or AST or ALT and
(iii) Urinary β-NAG, and
(iv) Leukocytes, or Neutrophils and
(v) alpha 2 macroglobulin, and optionally
(vi) hsa-miR-200, (in particular hsa-miR-200a and more particularly hsa-miR-200a-3p), fibrinogen and height.

In a particular embodiment of the invention, said kit comprises means for determining the level of:
(i) hsa-miR-34 (in particular hsa-miR-34a, more particularly miR-34a-5p), and
(ii) CK18-M65, and
(iii) Urinary β-NAG, and
(iv) Leukocytes, and
(v) alpha 2 macroglobulin and
(vi) hsa-miR-200, (in particular hsa-miR-200a and more particularly hsa-miR-200a-3p).

In another particular embodiment of the invention, said kit comprises means for determining the level of:
(i) hsa-miR-34 (in particular hsa-miR-34a, more particularly miR-34a-5p), and
(ii) CK18-M65, and
(iii) Urinary β-NAG, and
(iv) Leukocytes, and
(v) alpha 2 macroglobulin, and
(vi) Fibrinogen and
(vii) height.

The kit of the invention is useful for implementing the methods described above may further optionally include instructions for implementing said methods. The kit may comprise reagents and buffers appropriate for conducting measures of the levels of markers identified above. In particular, the kit may comprise antibodies specific for a protein to be quantified, and/or primers useful for quantifying micro-RNA levels, as well-known in the art.

According to another aspect the present invention also relates to different methods for classifying a patient.

Method of Treatment

The present invention further relates to a method for treating NASH in a subject, comprising:
(a) diagnosing NASH or determining the activity, the stage, or the severity of NASH in a subject, classifying a subject as a receiver or non receiver of a treatment for NASH, determining the efficacy of a medical treatment based on a drug assimilation, determining the progression or regression of the NASH and determining the outcome of a patient according to the methods provided above;
(b) administering a treatment for NASH to said subject based on step (a).

The present invention further relates to a method for treating NASH in a subject, comprising:
(a) classifying said subject according to the method of classification as defined above;

(b) administering a treatment for NASH to the subject if said subject is classified as receiver of the treatment according to step (a).

The present invention further relates to a method for managing low NASH activity, or moderate NASH in a subject, comprising:
(a) classifying said subject according to the method of classification as defined above;
(b) providing diet and/or lifestyle recommendations to the subject if said subject is classified as non receiver of the treatment according to step (a).

The method for treating NASH according to the present invention comprises the administration of one or more anti-NASH compound(s) to the subject in need thereof such as a compound of formula (I):

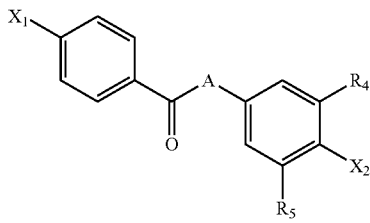

wherein:
X1 represents a halogen, a R1, or G1-R1 group;
A represents a CH=CH or a CH2—CH2 group;
X2 represents a G2-R2 group;
G1 and G2, identical or different, represent an atom of oxygen or sulfur;
R1 represents a hydrogen atom, an unsubstituted alkyl group, an aryl group or an alkyl group that is substituted by one or more halogen atoms, an alkoxy or an alkylthio group, cycloalkyl groups, cycloalkylthio groups or heterocyclic groups;
R2 represents an alkyl group substituted by at least a —COOR3 group, wherein R3 represents a hydrogen atom, or an alkyl group that is substituted or not by one or more halogen atoms, cycloalkyl groups, or heterocyclic groups.
R4 and R5, identical or different, representing an alkyl group that is substituted or not by one or more halogen atoms, cycloalkyl groups, heterocyclic groups;
or a pharmaceutically acceptable salt thereof.

In a particular embodiment of this method for the treatment of NASH, the compound of formula (I) is selected in the group consisting of 1-[4-methylthiophenyl]-3-[3,5-dimethyl-4-carboxydimethylmethyloxy phenyl]prop-2-en-1-one, 1-[4-methylthiophenyl]-3-[3,5-dimethyl-4-isopropyloxy carbonyldimethylmethyloxyphenyl]prop-2-en-1-one, 1-[4-methylthiophenyl]-3-[3,5-dimethyl-4-tertbutyloxycarbonyldimethylmethyloxyphenyl] prop-2-en-1-one, 1-[4-trifluoromethylphenyl]-3-[3,5-dimethyl-4-tertbutyloxycarbonyl dimethylmethyloxyphenyl]prop-2-en-1-one, 1-[4-trifluoromethylphenyl]-3-[3,5-dimethyl-4-carboxydimethylmethyloxyphenyl]prop-2-en-1-one, 1-[4-trifluoromethyl oxyphenyl]-3-[3,5-dimethyl-4-tertbutyloxycarbonyldimethylmethyloxy phenyl] prop-2-en-1-one, 1-[4-trifluoromethyloxyphenyl]-3-[3,5-dimethyl-4-carboxydimethylmethyl oxyphenyl]prop-2-en-1-one, 2-[2,6-dimethyl-4-[3-[4-(methylthio)phenyl]-3-oxo-propyl] phenoxy]-2-methylpropanoic acid, and 2-[2,6-dimethyl-4-[3-[4-(methylthio) phenyl]-3-oxo-propyl]phenoxy]-2-methylpropanoic acid isopropyl ester; or a pharmaceutically acceptable salt thereof.

In a further particular embodiment of the invention, the compound of formula (I) is 1-[4-methylthiophenyl]-3-[3,5-dimethyl-4-carboxydimethylmethyloxy phenyl]prop-2-en-1-one or a pharmaceutically acceptable salt thereof.

Other compounds that might be used in the method for the treatment of NASH of the present invention may include, without limitation, a compound selected from the following classes and specific compounds here after.

Illustrative, non-limiting, anti-NASH agents useful in the practice of the present invention include:
Acetyl-CoA carboxylase inhibitors;
Anti-LPS antibodies;
Apical sodium-codependent bile acid transporter inhibitors;
bioactive lipids;
Cannabinoid CB1 receptor antagonists;
Caspase inhibitors;
Cathepsin inhibitors;
CCR antagonists;
Diacylglycerol-O-acyltransferase (DGAT) inhibitors
Dipeptidyl peptidase IV (DPP4) inhibitors;
Dual NOX (NADPH oxidase) 1&4 inhibitors;
Extracellular matrix protein modulators;
Stearoyl CoA desaturase-1 inhibitors/fatty acid bile acid conjugates (FABAC);
Farnesoid X receptor (FXR) agonists;
Fibroblast Growth Factor 19 (FGF-19) recombinants;
Fibroblast Growth Factor 21 (FGF-21) agonists;
Galectin 3 inhibitors;
Glucagon-like peptide-1 (GLP-1) analogs;
G-protein coupled receptor (GPCR) modulators;
Integrin inhibitors;
Leukotriene (LT)/Phosphodiesterase (PDE)/Lipoxygenase (LO) inhibitors;
Macrolides;
miRNA antagonists;
Monoclonal antibodies;
mTOR modulators;
nuclear receptor ligands;
P2Y13 protein agonists;
Protease-activated receptor (PAR)-2 antagonists;
Protein kinase modulators;
PPAR alpha agonists;
PPAR gamma agonists;
PPAR delta agonists;
PPARalpha/gamma agonists;
PPARalpha/delta agonists;
PPAR gamma/delta;
PPAR alpha/gamma/delta agonists or PPARpan agonists;
Rho-associated protein kinase 2 (ROCK2) inhibitors;
signal-regulating kinase 1 (ASK1) inhibitors;
Sodium-glucose transport (SGLT) 2 inhibitors;
stearoyl CoA desaturase-1 inhibitors/fatty acid bile acid conjugates;
thyroid receptor β (THR β) agonists;
Toll Like Receptor 4 (TLR-4) antagonists;
Tyrosine kinase receptor (RTK) modulators;
Vascular adhesion protein-1 (VAP-1) inhibitors and Vitamin D receptor (VDR) agonists.

Other anti-NASH agents include KB-GE-001 and NGM-386 and NGM-395 and NC-10 and TCM-606F.

According to the invention, the term "acetyl-CoA carboxylase inhibitors" as used herein includes, but is not limited to GS-0976; ND-654; AC-8632; PF05175157.

According to the invention, the term "anti-LPS antibodies" as used herein includes, but is not limited to IMM-124-E.

According to the invention, the term "apical sodium-codependent bile acid transporter inhibitor" as used herein includes, but is not limited to A-4250; volixibat; maralixibat formely SHP-625; GSK-2330672; elobixibat; CJ-14199.

According to the invention, the term "bioactive lipids" as used herein includes, but is not limited to 5-hydroxyeicosapentaenoic acid (15-HEPE, DS-102).

According to the invention, the term "cannabinoid CB1 receptor antagonists" as used herein includes, but is not limited to namacizumab; GRC-10801; MRI-1569; MRI-1867; DBPR-211; AM-6527; AM-6545; NESS-11-SM; CXB-029; GCC-2680; TM-38837; Org-50189; PF-514273; BMS-812204; ZYO-1; AZD-2207; AZD-1175; otenabant ibipinabant; surinabant; rimonabant; drinabant; SLV-326; V-24343; O-2093.

According to the invention, the term "caspase inhibitors" as used herein includes, but is not limited to emricasan; belnacasan; nivocasan; IDN-7314; F-573; VX-166; YJP-60107; MX-1122; IDN-6734; TLC-144; SB-234470; IDN-1965; VX-799; SDZ-220-976; L-709049.

According to the invention, the term "cathepsin inhibitors" as used herein includes, but is not limited to VBY-376; VBY-825; VBY-036; VBY-129; VBY-285; Org-219517; LY3000328; RG-7236; BF/PC-18.

According to the invention, the term "CCR antagonists" as used herein includes, but is not limited to cenicriviroc (CCR2/5 antagonist); PG-092; RAP-310; INCB-10820; RAP-103; PF-04634817; CCX-872.

According to the invention, the term "diacylglycerol-O-acyltransferase inhibitors" as used herein includes, but is not limited to IONIS-DGAT2Rx formely ISIS-DGAT2Rx; LY-3202328; BH-03004; KR-69530; OT-13540; AZD-7687; ABT-046.

According to the invention, the term "dipeptidyl peptidase IV inhibitors" as used herein includes, but is not limited to evogliptin; vidagliptin; fotagliptin; alogliptin; saxagliptin; tilogliptin; anagliptin; sitagliptin; retagliptin; melogliptin; gosogliptin; trelagliptin; teneligliptin; dutogliptin; linagliptin; gemigliptin; yogliptin; betagliptin; imigliptin; omarigliptin; vidagliptin; denagliptin.

According to the invention, the term "dual NOX (NADPH oxidase) 1&4 inhibitors" as used herein includes, but is not limited to GKT-831 formely GKT137831; GKT-901.

According to the invention, the term "extracellular matrix protein modulators" as used herein includes, but is not limited to CNX-024; CNX-025; SB-030.

According to the invention, the term "Farnesoid X receptor (FXR) agonists" as used herein includes, but is not limited to obeticholic acid; GS-9674; LJN-452; EDP-305; AKN-083; INT-767; GNF-5120; LY2562175; INV-33; NTX-023-1; EP-024297; Px-103; SR-45023.

According to the invention, the term "Fibroblast Growth Factor 19 (FGF-19) recombinants" as used herein includes, but is not limited to NGM-282.

According to the invention, the term "Fibroblast Growth Factor 21 (FGF-21) agonists" as used herein includes, but is not limited to PEG-FGF21 formely BMS-986036; YH-25348; BMS-986171; YH-25723; LY-3025876; NNC-0194-0499.

According to the invention, the term "Galectin 3 inhibitors" as used herein includes, but is not limited to GR-MD-02; TD-139; ANG-4021; Galectin-3C; LJPC-201; TFD-100; GR-MD-03; GR-MD-04; GM-MD-01; GM-CT-01; GM-CT-02; Gal-100; Gal-200.

According to the invention, the term "Glucagon-like peptide-1 (GLP-1) analogs" as used herein includes, but is not limited to semaglutide liraglutide; exenatide; albiglutide; dulaglutide; lixisenatide; loxenatide; efpeglenatide; taspoglutide; MKC-253; DLP-205; ORMD-0901.

According to the invention, the term "G-protein coupled receptor (GPCR) modulators" as used herein includes, but is not limited to CNX-023.

According to the invention, the term "integrin inhibitors" as used herein includes, but is not limited to integrin inhibitors of Pliant Therapeutic; integrin inhibitors of Indalo Therapeutics; integrin inhibitors of St Louis University; ProAgio; GSK-3008348.

According to the invention, the term "leukotriene/phosphodiesterase/lipoxygenase inhibitors" as used herein includes, but is not limited to tipelukast (formely MN-001); tomelukast; sulukast; masilukast; zafirlukast; pranlukast; montelukast; gemilukast; verlukast; aklukast; pobilikast; cinalukast; iralukast.

According to the invention, the term "macrolides" as used herein includes, but is not limited to solithromycin; azithromycin; erythromycin.

According to the invention, the term "miRNA antagonists" as used herein includes, but is not limited to RG-125 formely AZD4076; RGLS-5040; RG-101; MGN-5804; MRG-201.

According to the invention, the term "metalloprotease-9 (MMP-9) stimulators" as used herein includes, but is not limited to MMP-9 stimulator of Elastomics Ab.

According to the invention, the term "monoclonal antibodies" as used herein includes, but is not limited to bertilimumab; NGM-313; IL-20 targeting mAbs; fresolimumab (antiTGFp) formely GC1008; timolumab formely BTT-1023; namacizumab; omalizumab; ranibizumab; bevacizumab; lebrikizumab; epratuzumab; felvizumab; matuzumab; monalizumab; reslizumab; inebilizumab.

According to the invention, the term "mTOR modulators" as used herein includes, but is not limited to MSDC-0602; AAV gene therapy co-administered with SVP-sirolimus.

According to the invention, the term "nuclear receptor ligands" as used herein includes, but is not limited to DUR-928 formely DV 928.

According to the invention, the term "P2Y13 protein agonists" as used herein includes, but is not limited to CER-209.

According to the invention, the term "protease-activated receptor (PAR)-2 antagonists" as used herein includes, but is not limited to PZ-235; NP-003.

According to the invention, the term "protein kinase modulators" as used herein includes, but is not limited to CNX-014; MB-11055; ALF-1; mangiferin; amlexanox; GS-444217; REG-101; valine.

According to the invention, the term "PPAR alpha agonists" as used herein includes, but is not limited to fenofibrate, ciprofibrate, pemafibrate, gemfibrozil, clofibrate, binifibrate, clinofibrate, clofibric acid, nicofibrate, pirifibrate, plafibride, ronifibrate, theofibrate, tocofibrate, SR10171;

According to the invention, the term "PPAR gamma agonists" as used herein includes, but is not limited to Pioglitazone, deuterated pioglitazone, Rosiglitazone, efatutazone, ATx08-001, OMS-405, CHS-131, THR-0921, SER-150-DN, KDT-501, GED-0507-34-Levo, CLC-3001, ALL-4.

According to the invention, the term "PPAR delta agonists" as used herein includes, but is not limited to GW501516 (Endurabol or ({4-[({4-methyl-2-[4-(trifluoromethyl)phenyl]-1,3-thiazol-5-yl}methyl)sulfanyl]-2- methylphenoxy}acetic acid)) or MBX8025 (Seladelpar or {2-methyl-4-[5-methyl-2-(4-trifluoromethyl-phenyl)-2H-[1,2,3]triazol-4-ylmethylsylfanyl]-phenoxy}-acetic acid) or GW0742 ([4-[[[2-[3-fluoro-4-(trifluoromethyl)phenyl]-4-methyl-5-thiazolyl]methyl]thio]-2-methyl phenoxy]acetic acid) or L165041 or HPP-593 or NCP-1046.

According to the invention, the term "PPAR alpha/gamma agonists" (also named glitazars) used herein includes, but is not limited to Saroglitazar, Aleglitazar, Muraglitazar, Tesaglitazar, DSP-8658.

In addition to elafibranor, illustrative PPAR alpha/delta agonists include, without limitation, T913659.

According to the invention, the term "PPAR gamma/delta agonist" used herein includes, but is not limited to a conjugated linoleic acid (CLA), T3D-959.

According to the invention, the term "PPAR alpha/gamma/delta agonists" or "PPARpan agonists" used herein includes, but is not limited to IVA337 or TTA (tetradecylthioacetic acid) or Bavachinin or GW4148 or GW9135, or Bezafibrate or Lobeglitazone, or CS038.

According to the invention, the term "Rho-associated protein kinase 2 (ROCK2) inhibitors" as used herein includes, but is not limited to KD-025; TRX-101; BA-1049; LYC-53976; INS-117548; RKI-1447.

According to the invention, the term "signal-regulating kinase 1 (ASK1) inhibitors" as used herein includes, but is not limited to GS-4997.

According to the invention, the term "sodium-glucose transport (SGLT) 2 inhibitors" as used herein includes, but is not limited to remogliflozin; dapagliflozin; empagliflozin; ertugliflozin; sotagliflozin; ipragliflozin; tianagliflozin; canagliflozin; tofogliflozin; janagliflozin; bexagliflozin; luseogliflozin; sergliflozin; HEC-44616; AST-1935; PLD-101.

According to the invention, the term "stearoyl CoA desaturase-1 inhibitors/fatty acid bile acid conjugates" as used herein includes, but is not limited to aramchol; GRC-9332; steamchol; TSN-2998; GSK-1940029; XEN-801.

According to the invention, the term "thyroid receptor β (THR β) agonists" as used herein includes, but is not limited to VK-2809; MGL-3196; MGL-3745; SKL-14763; sobetirome; BCT-304; ZYT-1; MB-07811; eprotirome.

According to the invention, the term "Toll Like Receptor 4 (TLR-4) antagonists" as used herein includes, but is not limited to naltrexone JKB-121; M-62812; resatorvid; dendrophilin; CS-4771; AyuV-1; AyuV-25; NI-0101; EDA-HPVE7; eritoran.

According to the invention, the term "tyrosine kinase receptor (RTK) modulators" as used herein includes, but is not limited to CNX-025; KBP-7018 According to the invention, the term "vascular adhesion protein-1 (VAP-1) inhibitors" as used herein includes, but is not limited to PXS-4728A; CP-664511; PRX-167700; ASP-8232; RTU-1096; RTU-007; BTT-1023.

According to the invention, the term "vitamin D receptor (VDR) agonists" as used herein includes, but is not limited to calciferol; alfacalcidol; 1,25-dihydroxyvitamin D3; Vitamin D2; Vitamin D3; calcitriol; Vitamin D4; Vitamin D5; dihydrotachysterol; calcipotriol; tacalcitol 1,24-dihydroxyvitamin D3; paricalcitol.

The present invention is also dedicated to other liver diseases, and more particularly fibrotic liver diseases such as: viral hepatitis (HBV, HCV,...), Alcoholic steatohepatitis, Biliary diseases (Primary biliary cholangitis, Primary Sclerosing cholangitis, Autoimmune hepatitis, Wilson's disease, Alpha1 antitrypsine deficiency).

EXAMPLES

Materials and Methods

Sample Collection and Analysis
Clinical Study

The clinical trial (phase 2 GOLDEN-505 trial in NASH (GFT505-212-7-NCT01694849) is a multicentre, randomized, double blind, placebo-controlled study to evaluate the efficacy and safety of Elafibranor (1-[4-methylthiophenyl]-3-[3,5-dimethyl-4-carboxydimethylmethyloxy phenyl]prop-2-en-1-one) once daily on steatohepatitis in patients with non-alcoholic steatohepatitis (NASH).

Liver biopsy was performed to confirm the diagnosis of NASH after appropriate exclusion of liver disease of other etiology. NASH was diagnosed as steatohepatitis evaluated by liver biopsy within 6 months before randomization. Steatohepatitis confirmation was based on central reading of liver biopsies. NASH patients were defined with a NAS ≥3 including steatosis score ≥1 and hepatocyte ballooning ≥1 and lobular inflammation ≥1.

The study was approved by appropriate regulatory bodies at each participating center and all patients had given consent for participation in medical research.

Plasma samples from the phase 2 GOLDEN-505 trial in NASH (were used to identify the most powerful and significant marker(s) of NASH.

Liver biopsy was performed to confirm the diagnosis of NASH after appropriate exclusion of liver disease of other etiology.

NASH was diagnosed as steatohepatitis evaluated by liver biopsy within 6 months before randomization. Steatohepatitis confirmation was based on central reading of liver biopsies.

The study was approved by appropriate regulatory bodies at each participating center and all patients had given consent for participation in medical research.

Blood Sampling and Laboratory Testing

Blood samples were collected according to the Central Laboratory Protocol and Manual—Genfit-GFT505-212-7.

According to the study protocol, following analyses were performed.

HEMATOLOGY includes hemoglobin, hematocrit, RBC count, leukocytes, differential leukocyte count (neutrophils, lymphocytes, eosinophils, monocytes, basophils -abs. and % values), platelets and reticulocytes.

BIOCHEMISTRY Panel I includes plasma glucose, triglycerides (TG), creatinine, creatinine clearance, gamma-glutamyltransferase (GGT), aspartate aminotransferase (AST), alanine aminotransferase (ALT), creatine phosphokinase (CPK), alkaline phosphatase, thyroid stimulating hormone (TSH) and HbA1c.

BIOCHEMISTRY Panel II includes plasma glucose, creatinine, creatinine clearance, total protein, albumin, sodium, potassium, chloride, calcium, uric acid, urea expressed as blood urea nitrogen (BUN), aspartate aminotransferase (AST), alanine aminotransferase (ALT), gamma-glutamyltransferase (GGT), alkaline phosphatase, creatine phosphokinase (CPK), bilirubin total, bilirubin conjugated, C-reactive protein (hsCRP), AST/ALT Ratio and HbA1c.

URINALYSIS includes:
  Dipstick analysis (specific gravity, pH, RBC, leukocytes, glucose, protein, ketones, bilirubin, urobilinogen and nitrite)

Microscopy analysis includes RBC, WBC, casts, crystals, bacteria, epithelial cells and yeasts.

Chemistry analysis (albumin and creatinine)

SEROLOGY includes HIV ab I/II, HCV ab, HCV RNA (only tested upon receipt of HCV RNA Visit samples and in case of 'reactive' or 'indeterminate' result for HCV Ab) and HbsAg.

LIPID PANEL includes triglycerides (TG), total cholesterol, non HDL-C (calculation), high-density lipoprotein cholesterol (HDL-C), low density lipoprotein (LDL-C) (calculation), calculated very low density lipoprotein cholesterol (VLDL-C) (calculation), apolipoprotein Al (ApoAl) and apolipoprotein B (ApoB).

URINE CHEMISTRY includes alpha-1-microglobulin, beta-N-acetylglucosaminidase(beta-NAG) and neutrophil-gelatinase associated lipocalin(N-Gal)

SAFETY MARKERS includes homocysteine, NT-ProBNP, Troponin T, Cystatin C, and Beta2-microglobulin.

GLYCEMIC AND OTHER LIPIDIC PARAMETERS includes leptin, insulin, homeostatic model assessment (HOMA-IR), serum glucose (for calculation of HOMA-IR), fructosamine, C-peptide and free fatty acids (FFA).

INFLAMMATORY MARKERS includes haptoglobin, fibrinogen, tumor necrosis factor alpha (TNF-α), interleukine 6 (IL-6) and plasminogen activator inhibitor 1 (PAI-1) Ag (citrate).

LIVER MARKERS includes cytokeratin-18 (CK18) (M65 & M30), adinopectin, ferritin, alpha2 macroglobulin, FGF19 & FGF21, hyaluronic acid (Advia centaur, reagentiaprocured by Siemens Belgium and charged to Genfit in pass-through), N-terminal pro-peptide of collagen type III (PIIINP) (Advia centaur, reagentia procured by Siemens Belgium) and tissue inhibitor of matrix metalloprotease-1 (TIMP-1) (Advia centaur, reagentiaprocured by Siemens).

The list of methods, instrument and manufacturer for each biochemical assay is reported in this table:

Sample Collection & Storage

Blood samples used in this biomarker study were drawn from patients of the 505.212.7 study before treatment period. Written, informed consent for collection, storage and use of additional samples was obtained from every patient.

Blood collected in citrate containing tubes 2.7 mL was processed by separating cell-free plasma from blood cells within 15 minutes of collection by centrifugation at 1,500×g for 15 minutes. The supernatant plasma was transferred to a new tube. Tubes were kept at −70° C.

To proceed to RNA extraction, plasma tubes were then centrifuged at 13,000×g for 2 min to pellet and remove the platelets. The supernatant platelet-free plasma was transferred to a new tube, frozen in liquid nitrogen and stored at −80° C.

Total RNA Extraction and Quantitation of miRNA in Citrated Plasma

Total RNA with preserved miRNAs was extracted from 400 μl of platelet-free plasma by miRNeasy extraction kit (miRNeasy Serum/Plasma Kit (cat. no. 217184)) and using a plasma/QIAzol ratio of 1:5 according to the manufacturer's instructions. Synthetic spiked-in C. elegans miR-39 was added to the samples [3,125 fmoles] prior to RNA extraction as internal control of RNA extraction process. The elution was performed in 18 μl of elution buffer.

Expression of mature miRNAs was detected according to the manufacturer's instructions using the Taqman miRNA qRT-PCR Assay: TaqMan MicroRNA Reverse transcription Kit (Ref: 4366596, Applied Biosystems, Carlsbad, CA), TaqMan MicroRNA Assay 20×(Ref: 4440887, Applied Biosystems) and TaqMan Universal Master Mix II (Ref: 4440040, Applied Biosystems).

Reverse Transcription were performed using a GeneAmp® PCR System 9700 thermal cycler (Ref: 200005, Applied Biosystems) with cycling conditions of 16° C. for 30 minutes followed by 42° C. for 30 minutes and 85° C. for 5 minutes before holding at 4° C. The Reverse transcription

| Parameter | Method | Instrument | Manufacturer |
| --- | --- | --- | --- |
| leptin | ELISA | manually | R&D systems |
| insulin | CLIA | Immulite 2000 | Siemens |
| HOMA-IR | Calculation with Glucose and Insulin | | |
| fructosamine | Colorimetric | Modular P800 | Roche Diagnostics |
| c-Peptide | CLIA | Immulite 2000 | Siemens |
| haptoglobin | immunoturbidimetry | Modular P800 | Roche Diagnostics |
| fibrinogen | Clauss method | STAR-evolution | Stago |
| TNF alpha | fluorokine multi analyte profiling | Luminex | Millipore |
| IL-6 | fluorokine multi analyte profiling | Luminex | Millipore |
| PAI-1 Ag | ELISA | manually | Stago |
| FFA | ACS-ACOD | Modular P800 | Roche Diagnostics |
| CK18 M30 | ELISA | manually | Peviva |
| CK18 M65 | ELISA | manually | Peviva |
| adiponectin | ELISA | manually | Millipore |
| ferritin | ECLIA | Modular E170 | Roche Diagnostics |
| alpha2 macroglobulin | nephelometry | BN II | Siemens |
| hyaluronic acid | immunoassay | Advia centaur | Siemens |
| PIIINP | immunoassay | Advia centaur | Siemens |
| TIMP-1 | immunoassay | Advia centaur | Siemens |
| FGF-19 | ELISA | manually | R&D systems |
| FGF-21 | ELISA | manually | R&D systems |
| visfatin | ELISA | manually | Alpco immunoassays |
| resistin | ELISA | manually | R&D systems |
| YKL40, CHi3L1 | Human Chitinase 3-like 1 Immunoassay Quantikine ® ELISA Catalog Number DC3L10 For the quantitative determination of human Chitinase 3-like 1 (CHI3L1) concentrations in cell culture supernates, serum, plasma, and urine. | | | was multiplexed with 4 miRNA specific-reverse primers in order to conserve RNA sample.

Quantitative PCR were performed using a CFX96™ Real-Time System (C1000 Touch™ Thermal Cycler, Bio-Rad) with cycling conditions of 95° C. for 10 minutes followed by 95° C. for 15 sec and 60° C. for 60 sec for a total of 50 cycles and 30° C. for 30 sec.

The sequences of specific primers for miRNA of potential interest were chosen according to the following table 2.

TaqMan MicroRNA Assay 20×(Ref: 4440887, Applied Biosystems) and TaqMan Universal Master Mix II (Ref: 4440040, Applied Biosystems).

Reverse Transcription were performed using a GeneAmp® PCR System 9700 thermal cycler (Ref: 200005, Applied Biosystems) with cycling conditions of 16° C. for 30 minutes followed by 42° C. for 30 minutes and 85° C. for 5 minutes before holding at 4° C. The Reverse transcription

TABLE 2 sequences of tested miRNA

| Mature miRNA | Assay id (Life Technologies) | Sequence of mature miRNA | mirBase number | Supplier |
| --- | --- | --- | --- | --- |
| cel-miR-39-3p | 000200 | UCACCGGGUGUAAAUCAGCUUG (SEQ ID NO: 1) | MIMAT0000010 | Life technologies |
| hsa-miR-122-5p | 002245 | UGGAGUGUGACAAUGGUGUUUG (SEQ ID NO: 2) | MIMAT0000421 | Life technologies |
| hsa-miR-34a-5p | 000426 | UGGCAGUGUCUUAGCUGGUUGU (SEQ ID NO: 3) | MIMAT0000255 | Life technologies |
| hsa-miR-200a-3p | 000502 | UAACACUGUCUGGUAACGAUGU (SEQ ID NO: 4) | MIMAT0000318 | Life technologies |
| hsa-miR-29b-3p | 000413 | UAGCACCAUUUGAAAUCAGUGUU (SEQ ID NO: 5) | MIMAT0000100 | Life technologies |
| hsa-miR-192-5p | 000491 | CUGACCUAUGAAUUGACAGCC (SEQ ID NO: 6) | MIMAT0000222 | Life technologies |
| hsa-miR-221-3p | 000524 | AGCUACAUUGUCUGCUGGGUUUC (SEQ ID NO: 7) | MIMAT0000278 | Life technologies |
| hsa-miR-103a-3p | 000439 | AGCAGCAUUGUACAGGGCUAUGA (SEQ ID NO: 8) | MIMAT0000101 | Life technologies |
| hsa-miR-155-5p | 002623 | UUAAUGCUAAUCGUGAUAGGGGU (SEQ ID NO: 9) | MIMAT0000646 | Life technologies |
| hsa-miR-199a-5p | 000498 | CCCAGUGUUCAGACUACCUGUUC (SEQ ID NO: 10) | MIMAT0000231 | Life technologies |

Data used in the construction of the algorithm were in Cq format. The Cq Determination mode was Regression.

Total RNA Extraction and Quantitation of miRNA in Serum.

Serum Total RNA with preserved miRNAs was extracted from 100 μl of serum by miRVanaParis extraction kit (AM1556, Ambion) according to the manufacturer's instructions. Synthetic spiked-in *C. elegans* miR-39 was added to the samples [3,125 fmoles](MSY0000010, Qiagen) prior to RNA extraction as internal control of RNA extraction process. The elution was performed in 100 μl of elution buffer.

Expression of mature miRNAs was detected according to the manufacturer's instructions using the Taqman miRNA qRT-PCR Assay: TaqMan MicroRNA Reverse transcription Kit (Ref: 4366596, Applied Biosystems, Carlsbad, CA), was multiplexed with 4 miRNA specific-reverse primers in order to conserve precious RNA sample.

Quantitative PCR were performed using a CFX96™ Real-Time System (01000 Touch™ Thermal Cycler, Bio-Rad) with cycling conditions of 9500 for 10 minutes followed by 95° C. for 15 sec and 60° C. for 60 sec for a total of 50 cycles and 30° C. for 30 sec.

The sequences of specific primers for miRNA of interest were chosen according to the following table:

| Mature miRNA | Assay id | Sequence of mature miRNA | mirBase number | Supplier |
|---|---|---|---|---|
| cel-miR-39-3p | 000200 | UCACCGGGUGUAAAUCAGCUUG | MIMAT0000010 | Life technologies |
| hsa-miR-122-5p | 002245 | UGGAGUGUGACAAUGGUGUUUG | MIMAT0000421 | Life technologies |
| hsa-miR-34a-5p | 000426 | UGGCAGUGUCUUAGCUGGUUGU | MIMAT0000255 | Life technologies |
| hsa-miR-200a-3p | 000502 | UAACACUGUCUGGUAACGAUGU | MIMAT0000318 | Life technologies |
| hsa-miR-29b-3p | 000413 | UAGCACCAUUUGAAAUCAGUGUU | MIMAT0000100 | Life technologies |
| hsa-miR-192-5p | 000491 | CUGACCUAUGAAUUGACAGCC | MIMAT0000222 | Life technologies |
| hsa-miR-221-3p | 000524 | AGCUACAUUGUCUGCUGGGUUUC | MIMAT0000278 | Life technologies |
| hsa-miR-103a-3p | 000439 | AGCAGCAUUGUACAGGGCUAUGA | MIMAT0000101 | Life technologies |
| hsa-miR-155-5p | 002623 | UUAAUGCUAAUCGUGAUAGGGGU | MIMAT0000646 | Life technologies |
| hsa-miR-199a-5p | 000498 | CCCAGUGUUCAGACUACCUGUUC | MIMAT0000231 | Life technologies |

Synthetic hsa-miRNAs (Integrated DNA Technologies) were diluted at 3.125 fmol/mL and 5 µL were used for reverse transcription concurrently with RNA extracted from serum samples. The product was serially diluted and PCR was performed on all samples (standards and serum-derived RNA). Standard curve was performed in duplicate and used to convert Cq data in copies/µL. The Cq Determination mode was Regression. Data used in the construction of the algorithm were in Log 10(copies/µL of serum) format.

| Ref.ID | Oligoribo-nucleotide | Single strand RNA Sequence | MW | Tm (° C.) | GC content (%) | Supplier |
|---|---|---|---|---|---|---|
| 69861876 | cel-miR-39-3p | 5'Phos-UCACCGGGUGUAAAUCAGCUUG-3' | 7098.2 | 53.2 | 50.0 | IDT |
| 69861877 | hsa-miR-122-5p | 5'Phos-UGGAGUGUGACAAUGGUGUUUG-3' | 7196.2 | 50.7 | 45.5 | IDT |
| 69861878 | hsa-miR-29b-3p | 5'Phos-UAGCACCAUUUGAAAUCAGUGUU-3' | 7373.4 | 44.9 | 34.8 | IDT |
| 69861879 | hsa-miR-34a-5p | 5'Phos-UGGCAGUGUCUUAGCUGGUUGU-3' | 7109.1 | 53.0 | 50.0 | IDT |
| 69861880 | hsa-miR-192-5p | 5'Phos-CUGACCUAUGAAUUGACAGCC-3' | 6376.0 | 53.4 | 47.6 | IDT |
| 69861881 | hsa-miR-221-3p | 5'Phos-AGCUACAUUGUCUGCUGGGUUUC-3' | 7358.3 | 51.8 | 47.8 | IDT |
| 69861882 | hsa-miR-103a-3p | 5'Phos-AGCAGCAUUGUACAGGGCUAUGA-3' | 7490.5 | 59.4 | 47.8 | IDT |

-continued

| Ref. ID | Oligoribo-nucleotide | Single strand RNA Sequence | MW | Tm (° C.) | GC content (%) | Supplier |
|---|---|---|---|---|---|---|
| 69861883 | hsa-miR-155-5p | 5'Phos-UUAAUGCUAAUCGUGAUAGGGGU-3' | 7469.4 | 50.7 | 39.1 | IDT |
| 69861884 | hsa-miR-199a-5p | 5'Phos-CCCAGUGUUCAGACUACCUGUUC-3' | 7300.3 | 51.9 | 52.2 | IDT |
| 69861885 | hsa-miR-200a-3p | 5'Phos-UAACACUGUCUGGUAACGAUGU-3' | 7083.2 | 51.3 | 40.9 | IDT |

Statistical Analysis

Objective and Definition

The objective of these analyses was to discover biomarkers that can be related to the identification of NASH patients to be treated. Patients to be treated (TBT) are defined differently according to the different parts of the study.

Accordincg to the first aspect of the invention, TBT are defined as:
steatosis score ≥1
hepatocyte ballooning score ≥1
lobular inflammation score ≥1
NAS (NAFLD Activity Score) ≥4 (NAS is defined as the sum of the steatosis score, hepatocyte ballooning score and lobular inflammation score)
fibrosis stage ≥2 (such as a fibrosis stage equal to 2, 3 or 4, in particular 2 or 3).

According to the second aspect of the invention, TBT are defined as:
steatosis score ≥1
hepatocyte ballooning score ≥1
lobular inflammation score ≥1
NAS (NAFLD Activity Score) ≥4 (NAS is defined as the sum of the steatosis score, hepatocyte ballooning score and lobular inflammation score)
fibrosis stage ≥1 (such as a fibrosis stage equal to 1, 2, 3 or 4).

According to the third aspect of the invention, TBT are defined as:
steatosis score ≥1
hepatocyte ballooning score ≥1
lobular inflammation score ≥1
NAS (NAFLD Activity Score) ≥4 (NAS is defined as the sum of the steatosis score, hepatocyte ballooning score and lobular inflammation score)
fibrosis stage=1b, 1c, 2, 3 or 4.

Other patients were stated as not to be treated (NTBT). For the analysis, TBT patients were categorized as 1 and NTBT as 0 in the response variable. As shown above, explicative variables encompassed a wide range of biomarkers measured in blood (hematology, biochemistry, coagulation, liver markers, circulating miRNA) or in urinary (dipstick, sediment) samples, as long as demographic (age, sex, race), region (study centre, country, continent) or medical (diabetes) recordings.

Dataset Management

The dataset used in this study was coming from the Golden-505 trial and was initially composed of 274 patients and 121 variables. The dataset management included the following steps:

1. Removal of patients without miRNAs measurement
2. Removal of variables with more than 10 missing values
3. Removal of patients with extreme values and 28 with remaining missing values It resulted in a dataset with 216 patients for all methods of the present invention, excepted for the methods concerning the serum which were done on 212 patients, and 112 variables that were used to test collinearity between explicative variables.

Test of Collinearity

Pearson correlation was calculated two by two between quantitative variables. When two variables presented a correlation superior to 0.7 for analysis using plasma miRNA or 0.6 for analysis using serum miRNA, univariate test of difference in their mean in relation to the response variable defining patients TBT were done. The selected variable was the more significant.

The collinear and selected variables are presented in Tables 3 to Tables 8.

These variables are dependent of the patient definition and thus are susceptible to vary from one category of patients to another.

Median Model

The median modelling process starts with the sampling of the dataset in a training set corresponding to 2/3 of TBT/NTBT patients and a validation set corresponding to the remaining 1/3 of TBT/NTBT patients. This sampling is performed randomly a million times and samples that present homogeneity between the training and validation sets (no significant difference in all explanatory variables between the two sets) are kept for analysis. A logistic generalised linear model of the response variable (defining TBT/NTBT patients) in relation to explanatory variables (biomarkers) is computed in each training set. For each training set model, a backward variable selection is performed and the optimal model is found by the lowest Akaike Index Criterion (AIC). Therefore, all explanatory variables have a model coefficient for each training set. The median algorithm is constructed using variables that show median coefficient different from zero and their corresponding coefficients. This algorithm is validated (calculation of ROC, AUC, optimal threshold, total accuracy, sensitivity, specificity, positive predictive value and negative predictive value) in each validation set and a median optimal threshold is obtained. For comparison with the bootstrap model, the median model is also applied in the overall dataset for validation.

Bootstrap Model

In the bootstrap modelling process, a logistic generalised linear model of the response variable (defining TBT/NTBT patients) in relation to explanatory variables (biomarkers) is computed on all patients from the overall dataset. A backward variable selection is done and the optimal algorithm is selected using AIC. The significance of variable coefficients from this optimal algorithm is then tested by running the algorithm using 1000 bootstrap samples. Coefficients that show 95% confidence interval excluding zero are considered significant. The algorithm is then validated by calculating ROC, AUC, optimal threshold, total accuracy, sensitivity, specificity, positive predictive value and negative predictive value.

Comparison to Other NASH Scoring Methods

Methods to establish NASH scores were previously described in literature:
  NAFLD Fibrosis Score (Angulo Index) (Angulo et al, 2007)
  ELF (Guha et al, 2008) (see also the ELF specification sheet healthcare.siemens.com/clinical-specialities/liver-disease/elf-test-now-avail)
  Fibrotest (Ratziu et al, 2006)
  Fibrometer (Cales et al, 2009)
  FLI (Bedogni et al, 2006)
  Steatosis score or SteatoTest (Poynard et al, 2005)

The inventors thus evaluated the NASH score of the invention using a number of these previous methods.

The comparison between the scores of the different models of the present invention versus other scores and the comparison between the scores of the different models of the present invention versus individual variables are presented in the tables 9 to 13.

The data presented herein show a spectacular improvement of the accuracy of the identification of NASH patients, or potential NASH patients, determination of NASH activity, stage or severity. This finding is of outmost importance and will be an invaluable tool to improve patient management efficiency.

TABLE 3

Selected and dropped variables in collinearity test for patient at risk to be treated corresponding to the following liver biopsy-derived grades: steatosis score ≥ 1, hepatocyte ballooning score ≥ 1, lobular inflammation score ≥ 1, NAS (NAFLD Activity Score) ≥ 4 and fibrosis stage ≥ 2 (such as a fibrosis stage equal to 2, 3 or 4, in particular 2 or 3) with measurement in plasma

| Selected variables in collinear variables | Dropped variables in collinear variables | | |
|---|---|---|---|
| bmi | waist | weight | |
| HOMA | Insuline | C-Peptide | |
| CK18-M65 | CK18-M30 | AST | ALT |
| HBA1C | Fasting glucose plasma | Fructosamine | Fasting glucose serum |
| Basophils (abs) | Basophils (%) | | |
| Eosinophils (abs) | Eosinophils (%) | | |
| Hematocrit | Hemoglobin | RBC Count | |
| Leukocytes | Neutrophils (abs) | | |
| Neutrophils (%) | Lymphocytes (%) | | |
| Prothrombin time (sec) | INR | Prothrombin time (%) | |
| Reticulocytes (abs.) | Reticulocytes (% of RBC) | | |
| High-density lipoprotein (HDL) | high-density lipoprotein cholesterol (HDL-C) | Apolipoprotein AI (Apo AI) | |
| Intermediate-density lipoprotein C | Total cholesterol | Apolipoprotein B (Apo B) | Non HDL-C |
| Low Density Lipoprotein (LDL) 1 | Intermediate-density lipoprotein A | | |
| Low Density Lipoprotein (LDL) 2 | Apolipoprotein B (Apo B) | Non HDL-C | |
| Very Low Density Lipoprotein Cholesterol | Triglycerides | | |
| miRNA103 | miRNA155 | miRNA199a | miRNA221 |
| miRNA34a | miRNA122 | miRNA192 | |
| Urinary specific gravity | Urinary creatinine | | |

TABLE 4

Selected and dropped variables in collinearity test for patient at risk to be treated corresponding to the following liver biopsy-derived grades: steatosis score ≥ 1, hepatocyte ballooning score ≥ 1, lobular inflammation score ≥ 1, NAS (NAFLD Activity Score) ≥ 4 and fibrosis stage ≥ 2 (such as a fibrosis stage equal to 2, 3 or 4, in particular 2 or 3) with measurement in sera (miRNA in copy/µL log 10)

| Selected variables in collinear variables | Dropped variables in collinear variables | | |
|---|---|---|---|
| bmi | waist | weight | |
| HOMA | Insuline | C-Peptide | |
| CK18-M65 | CK18-M30 | AST | ALT |
| FGF-21 | Homocysteine | | |
| Bilirubin conjugated | Bilirubin total | | |
| Cl | Na | | |

TABLE 4-continued

Selected and dropped variables in collinearity test for patient at risk to be treated corresponding to the following liver biopsy-derived grades: steatosis score ≥ 1, hepatocyte ballooning score ≥ 1, lobular inflammation score ≥ 1, NAS (NAFLD Activity Score) ≥ 4 and fibrosis stage ≥ 2 (such as a fibrosis stage equal to 2, 3 or 4, in particular 2 or 3) with measurement in sera (miRNA in copy/µL log 10)

| Selected variables in collinear variables | Dropped variables in collinear variables | | | |
|---|---|---|---|---|
| HBA1C | Fasting glucose plasma | Fructosamine | Fasting glucose serum | |
| Basophils (abs) | Basophils (%) | | | |
| Eosinophils (abs) | Eosinophils (%) | | | |
| Hematocrit | Hemoglobin | RBC Count | | |
| Leukocytes | Neutrophils (abs) | neutrophils (%) | | |
| Lymphocytes (%) | Neutrophils (%) | | | |
| Monocytes (abs.) | Monocytes (%) | | | |
| Prothrombin time (sec) | INR | Prothrombin time (%) | | |
| Reticulocytes (% of RBC) | Reticulocytes (abs.) | | | |
| High-density lipoprotein (HDL) | high-density lipoprotein cholesterol (HDL-C) | Apolipoprotein Al (Apo Al) | | |
| Intermediate-density lipoprotein A | Low Density Lipoprotein (LDL) 1 Non HDL-C | Total cholesterol | Apolipoprotein B (Apo B) | Intermediate-density lipoprotein B |
| Intermediate-density lipoprotein C | Intermediate-density lipoprotein B | Total cholesterol | Non HDL-C | Apolipoprotein B (Apo B) |
| Low Density Lipoprotein (LDL) 2 | Total cholesterol | Non HDL-C | Apolipoprotein B (Apo B) | |
| Very Low Density Lipoprotein Cholesterol | Triglycerides | Non HDL-C | | |
| miRNA34a | CK18-M30 | AST | miRNA122 | |
| Urinary β-NAG | Urinary A1M | | | |

TABLE 5

Selected and dropped variables in collinearity test for patient at risk to be treated corresponding to the following liver biopsy-derived grades: steatosis score ≥ 1, hepatocyte ballooning score ≥ 1, lobular inflammation score ≥ 1, NAS (NAFLD Activity Score) ≥ 4 and fibrosis stage ≥ 2 (such as a fibrosis stage equal to 2, 3 or 4, in particular 2 or 3) with measurement in sera (miRNA in Cq)

| Selected variables in collinear variables | Dropped variables in collinear variables | | | |
|---|---|---|---|---|
| bmi | waist | weight | | |
| HOMA | Insuline | C-Peptide | | |
| FGF-21 | Homocysteine | | | |
| Bilirubin conjugated | Bilirubin total | | | |
| Cl | Na | | | |
| HBA1C | Fasting glucose plasma | Fructosamine | Fasting glucose serum | |
| Basophils (abs) | Basophils (%) | | | |
| Eosinophils (abs) | Eosinophils (%) | | | |
| Hematocrit | Hemoglobin | RBC Count | | |
| Leukocytes | Neutrophils (abs) | Neutrophils (%) | | |
| Lymphocytes (%) | Neutrophils (%) | | | |
| Monocytes (abs.) | Monocytes (%) | | | |
| Prothrombin time (sec) | INR | Prothrombin time (%) | | |
| Reticulocytes (% of RBC) | Reticulocytes (abs.) | | | |
| High-density lipoprotein (HDL) | high-density lipoprotein cholesterol (HDL-C) | Apolipoprotein Al (Apo Al) | | |
| Intermediate-density lipoprotein A | Low Density Lipoprotein (LDL) 1 Non HDL-C | Total cholesterol | Apolipoprotein B (Apo B) | Intermediate-density lipoprotein B |
| Intermediate-density lipoprotein C | Intermediate-density lipoprotein B | Total cholesterol | Non HDL-C | Apolipoprotein B (Apo B) |
| Low Density Lipoprotein (LDL) 2 | Total cholesterol | Non HDL-C | Apolipoprotein B (Apo B) | |
| Very Low Density Lipoprotein Cholesterol | Triglycerides | Non HDL-C | | |
| miRNA34a | CK18-M30 CK18-M65 | AST | ALT | miRNA122 |
| Urinary β-NAG | Urinary A1M | | | |

TABLE 6

Significant selected and dropped variables in collinearity test for patient at risk to be treated corresponding to the following liver biopsy-derived grades: steatosis score ≥ 1, hepatocyte ballooning score ≥ 1, lobular inflammation score ≥ 1, NAS (NAFLD Activity Score) ≥ 4 and fibrosis stage ≥ 2 (such as a fibrosis stage equal to 2, 3 or 4, in particular 2 or 3) with measurement in sera (miRNA in copy/μL and log10 transformation)

| Significant selected variables in collinear variables | Dropped variables in collinear variables | | | |
|---|---|---|---|---|
| log10(HOMA) | Insuline | C-Peptide | | |
|  | HBA1C | Fasting glucose plasma | log10 (Fructosamine) | Fasting glucose serum |
| Prothrombin time (sec) | INR | Prothrombin time (%) | | |
| CK18-M65 | log10(CK18-M30) | log10(AST) | | |
| log10(miRNA34a) | log10(miRNA122) | log10(ALT) | log10(AST) | log10(CK18-M30) |

TABLE 7

Selected and dropped variables in collinearity test for patient at risk to be treated corresponding to the following liver biopsy-derived grades: steatosis score ≥ 1, hepatocyte ballooning score ≥ 1, lobular inflammation score ≥ 1, NAS (NAFLD Activity Score) ≥ 4 and fibrosis stage ≥ 1 (such as a fibrosis stage equal to 2, 3 or 4, in particular 2 or 3) with measurement in plasma

| Selected variables in collinear variables | Dropped variables in collinear variables | | | | |
|---|---|---|---|---|---|
| bmi | waist | weight | | | |
| HOMA | Insuline | C-Peptide | | | |
| CK18-M65 | CK18-M30 | AST | ALT | | |
| HBA1C | Fasting glucose plasma | Fructosamine | Fasting glucose serum | | |
| Basophils (abs) | Basophils (%) | | | | |
| Eosinophils (abs) | Eosinophils (%) | | | | |
| Lymphocytes (%) | Neutrophils (%) | | | | |
| Neutrophils (abs) | Leukocytes | | | | |
| Prothrombin time (sec) | INR | Prothrombin time (%) | | | |
| RBC Count | Hemoglobin | Hematocrit | | | |
| Reticulocytes (abs.) | Reticulocytes (% of RBC) | | | | |
| high-density lipoprotein cholesterol (HDL-C) | High-density lipoprotein (HDL) | Apolipoprotein Al (Apo Al) | | | |
| Low Density Lipoprotein (LDL) 1 | Intermediate-density lipoprotein A | | | | |
| Low Density Lipoprotein (LDL) 2 | Non HDL-C | Intermediate-density lipoprotein C | Apolipoprotein B (Apo B) | Total cholesterol | Very Low Density Lipoprotein Cholesterol |
| miRNA221 | miRNA155 | miRNA199a | miRNA103 | | |
| miRNA34a | miRNA122 | miRNA192 | | | |
| Urinary specific gravity | Urinary creatinine | | | | |

TABLE 8

Selected and dropped variables in collinearity test for patient at risk to be treated corresponding to the following liver biopsy-derived grades: steatosis score ≥ 1, hepatocyte ballooning score ≥ 1, lobular inflammation score ≥ 1, NAS (NAFLD Activity Score) ≥ 4 and fibrosis stage ≥ 1 (such as a fibrosis stage equal to 2, 3 or 4, in particular 2 or 3) with measurement in plasma

| Selected variables in collinear variables | Dropped variables in collinear variables | | | |
|---|---|---|---|---|
| bmi | waist | weight | | |
| HOMA | Insuline | C-Peptide | | |
| CK18-M65 | CK18-M30 | AST | ALT | |
| HBA1C | Fasting glucose plasma | Fructosamine | Fasting glucose serum | |
| Basophils (abs) | Basophils (%) | | | |
| Eosinophils (abs) | Eosinophils (%) | | | |
| Hemoglobin | Hematocrit | RBC Count | | |
| Leukocytes | Neutrophils (abs) | | | |
| Lymphocytes (%) | Neutrophils (%) | | | |

TABLE 8-continued

Selected and dropped variables in collinearity test for patient at risk to be treated corresponding to the following liver biopsy-derived grades: steatosis score ≥ 1, hepatocyte ballooning score ≥ 1, lobular inflammation score ≥ 1, NAS (NAFLD Activity Score) ≥ 4 and fibrosis stage ≥ 1 (such as a fibrosis stage equal to 2, 3 or 4, in particular 2 or 3) with measurement in plasma

| Selected variables in collinear variables | Dropped variables in collinear variables | | |
|---|---|---|---|
| Prothrombin time (sec) | INR | Prothrombin time (%) | |
| Reticulocytes (% of RBC) | Reticulocytes (abs.) | | |
| High-density lipoprotein cholesterol (HDL-C) | High-density lipoprotein (HDL) | Apolipoprotein A1 (Apo A1) | |
| Intermediate-density lipoprotein C | Total cholesterol | Non HDL-C | Apolipoprotein B (Apo B) |
| Low Density Lipoprotein (LDL) 1 | Intermediate-density lipoprotein A | | |
| Low Density Lipoprotein (LDL) 2 | Non HDL-C | Apolipoprotein B (Apo B) | |
| Triglycerides | Very Low Density Lipoprotein Cholesterol | | |
| miRNA103 | miRNA155 | miRNA199a | miRNA221 |
| miRNA34a | miRNA122 | miRNA192 | |
| Urinary specific gravity | Urinary creatinine | | |

TABLE 9

Comparison between the scores of the models of the present invention versus other known models In models (miRNA measured in serum in copy/µL log10) for patient at risk to be treated corresponding to the following liver biopsy-derived grades: steatosis score ≥1, hepatocyte ballooning score ≥1, lobular inflammation score ≥1, NAS (NAFLD Activity Score) ≥4 and fibrosis stage ≥2 (such as a fibrosis stage equal to 2, 3 or 4, in particular 2 or 3

| | AUC | Cut-off | Accuracy | Sensitivity | Specificity | PPV | NPV |
|---|---|---|---|---|---|---|---|
| Bootstrap | 0.82 | 0.4255 | 75.94 | 73.12 | 78.15 | 72.34 | 78.81 |
| Derived median model | 0.82 | 0.3201 | 75.94 | 72.04 | 78.99 | 72.83 | 78.33 |
| NAFLD Fibrosis Score | 0.69 | 0.676 | 34.12 | 66.67 | 8.47 | 36.47 | 24.39 |
| ELF | 0.70 | 7.7 | 45.28 | 97.28 | 4.20 | 44.39 | 71.43 |
| FibroTest | 0.68 | 0.48 | 66.51 | 40.86 | 86.55 | 70.37 | 65.19 |
| BARD | 0.64 | 2 | 59.91 | 60.22 | 59.66 | 53.85 | 65.74 |
| APRI | 0.72 | 1 | 66.51 | 26.88 | 97.48 | 89.29 | 63.04 |
| Non-Invasive Scoring System | 0.68 | 0.361 | 62.26 | 67.74 | 57.98 | 55.75 | 69.70 |
| FIB-4 | 0.72 | 3.25 | 58.96 | 6.45 | 100.00 | 100.00 | 57.77 |
| NAFLD Diag. Panel - NASH | 0.71 | 0.3641 | 71.70 | 63.44 | 78.15 | 69.41 | 73.23 |

Both models derived from the bootstrap and median models of the present invention have better AUC than the other known models. The differences are significantly demonstrating the interest of the present invention.

TABLE 10

Comparison between the scores of the boostrap models of the present invention versus other scores In models (miRNA measured in serum in copy/µL log10) for patient at risk to be treated corresponding to the following liver biopsy-derived grades: steatosis score ≥ 1, hepatocyte ballooning score ≥ 1, lobular inflammation score ≥ 1, NAS (NAFLD Activity Score) ≥ 4 and fibrosis stage ≥ 2 (such as a fibrosis stage equal to 2, 3 or 4, in particular 2 or 3)

| Score | AUC | Score | AUC | P-value |
|---|---|---|---|---|
| Bootstrap model | 0.82 | Derived median model | 0.82 | 0.7968 |
| Bootstrap model | 0.82 | NAFLD Fibrosis Score | 0.69 | 0.006184 |
| Bootstrap model | 0.82 | ELF | 0.70 | 0.01356 |
| Bootstrap model | 0.82 | Fibro Test | 0.68 | 0.007507 |
| Bootstrap model | 0.82 | BARD | 0.64 | 5.16E−05 |
| Bootstrap model | 0.82 | APRI | 0.72 | 0.03062 |
| Bootstrap model | 0.82 | Non-Invasive Scoring System (NISS) | 0.68 | 0.002862 |
| Bootstrap model | 0.82 | FIB4 | 0.72 | 0.04898 |
| Bootstrap model | 0.82 | NAFLD Diagnostic Panel-NASH | 0.71 | 0.02169 |

For all bootstrap models presented in the present invention and corresponding to the patient at risk as described previously, the AUC scores are statistically better than the AUC scores obtained from other models.
The score obtained with the derived median model is similar to those obtained with the bootstrap model, which means that both models are relevant.
The interest of the present invention is demonstrated.

TABLE 11

Comparison between the scores of the
derived median models of the present invention versus other scores
In models (miRNA measured in serum in copy/µL log10) for patient at risk to be
treated corresponding to the following liver biopsy-derived grades: steatosis
score ≥ 1, hepatocyte ballooning score ≥ 1, lobular inflammation score ≥ 1,
NAS (NAFLD Activity Score) ≥ 4 and fibrosis stage ≥ 2 (such as a fibrosis
stage equal to 2, 3 or 4, in particular 2 or 3)

| Score | AUC | Score | AUC | P-value |
|---|---|---|---|---|
| Derived median model | 0.82 | Bootstrap model | 0.82 | 0.7968 |
| Derived median model | 0.82 | NAFLD Fibrosis Score | 0.69 | 0.006828 |
| Derived median model | 0.82 | ELF | 0.70 | 0.01561 |
| Derived median model | 0.82 | Fibro Test | 0.68 | 0.006284 |
| Derived median model | 0.82 | BARD | 0.64 | 0.000129 |
| Derived median model | 0.82 | APRI | 0.72 | 0.03337 |
| Derived median model | 0.82 | Non-Invasive Scoring System (NISS) | 0.68 | 0.003578 |
| Derived median model | 0.82 | FIB4 | 0.72 | 0.04829 |
| Derived median model | 0.82 | NAFLD Diagnostic Panel-NASH | 0.71 | 0.0223 |

For all derived median models presented in the present invention and corresponding to the patient at risk as described previously, the AUC scores are statistically better than the AUC scores obtained from other models.
The score obtained with the bootstrap model is similar to those obtained with the derived median model, which means that both models are relevant.
The interest of the present invention is demonstrated.

TABLE 12

Comparison between the scores of the bootstrap model
of the present invention versus individual variables
In models (miRNA measured in serum in copy/µL log10) for
patient at risk to be treated corresponding to the following liver
biopsy-derived grades: steatosis score ≥ 1, hepatocyte
ballooning score ≥ 1, lobular inflammation score ≥ 1,
NAS (NAFLD Activity Score) ≥ 4 and fibrosis stage 2 (such
as a fibrosis stage equal to 2, 3 or 4, in particular 2 or 3)

| Score | AUC | Score | AUC | P-value |
|---|---|---|---|---|
| Bootstrap model | 0.82 | miRNA 34a | 0.74 | 0.002699 |
| Bootstrap model | 0.82 | YKL40 | 0.71 | 0.00143 |
| Bootstrap model | 0.82 | HBA1C | 0.67 | 1.343e−05 |
| Bootstrap model | 0.82 | A2M | 0.71 | 0.001744 |

The AUC score for the bootstrap model corresponding to the patient at risk as described previously and combining several variables is statistically better than the AUC score obtained for the individual variables.
Thus the combination of several variables through a logistic function according to the present invention is better and more precise than the study of the variable alone.
The interest of the present invention is demonstrated.

TABLE 13

Comparison between the scores of the derived median model
of the present invention versus individual variables
In models (miRNA measured in serum in copy/µL log10) for patient at risk
to be treated corresponding to the following liver biopsy-derived grades:
steatosis score ≥ 1, hepatocyte ballooning score ≥ 1, lobular inflammation
score ≥ 1, NAS (NAFLD Activity Score) ≥ 4 and fibrosis stage ≥ 2
(such as a fibrosis stage equal to 2, 3 or 4, in particular 2 or 3)

| Score | AUC | Score | AUC | P-value |
|---|---|---|---|---|
| Derived median model | 0.82 | miRNA 34a | 0.74 | 0.001128 |
| Derived median model | 0.82 | YKL40 | 0.71 | 0.004108 |
| Derived median model | 0.82 | HBA1C | 0.67 | 1.199e−05 |
| Derived median model | 0.82 | A2M | 0.71 | 0.003032 |

The AUC score for the derived median model corresponding to the patient at risk as described previously and combining several variables is statistically better than the AUC score obtained for the individual variables.
Thus the combination of several variables through a logistic function according to the present invention is better and more precise than the study of the variable alone.
The interest of the present invention is demonstrated.

REFERENCES

Angulo P, Hui J M, Marchesini G, Bugianesi E, George J, Farrell G C, Enders F, Saksena S, Burt A D, Bida J P, Lindor K, Sanderson S O, Lenzi M, Adams L A, Kench J, Therneau T M, Day C P (2007) The NAFLD fibrosis score: a noninvasive system that identifies liver fibrosis in patients with NAFLD. *Hepatology* 45: 846-854

Bedogni G, Bellentani S, Miglioli L, Masutti F, Passalacqua M, Castiglione A, Tiribelli C (2006) The Fatty Liver Index: a simple and accurate predictor of hepatic steatosis in the general population. *BMC Gastroenterol* 6: 33

Cales P, Laine F, Boursier J, Deugnier Y, Moal V, Oberti F, Hunault G, Rousselet M C, Hubert I, Laafi J, Ducluzeaux P H, Lunel F (2009) Comparison of blood tests for liver fibrosis specific or not to NAFLD. *J Hepatol* 50: 165-173

Guha I N, Parkes J, Roderick P, Chattopadhyay D, Cross R, Harris S, Kaye P, Burt A D, Ryder S D, Aithal G P, Day C P, Rosenberg W M (2008) Noninvasive markers of fibrosis in nonalcoholic fatty liver disease: Validating the European Liver Fibrosis Panel and exploring simple markers. *Hepatology* 47: 455-460

Poynard T, Ratziu V, Naveau S, Thabut D, Charlotte F, Messous D, Capron D, Abella A, Massard J, Ngo Y, Munteanu M, Mercadier A, Manns M, Albrecht J (2005) The diagnostic value of biomarkers (SteatoTest) for the prediction of liver steatosis. *Comp Hepatol* 4: 10

Ratziu V, Massard J, Charlotte F, Messous D, Imbert-Bismut F, Bonyhay L, Tahiri M, Munteanu M, Thabut D, Cadranel J F, Le Bail B, de Ledinghen V, Poynard T (2006) Diagnostic value of biochemical markers (FibroTest-FibroSURE) for the prediction of liver fibrosis in patients with non-alcoholic fatty liver disease. *BMC Gastroenterol* 6: 6

The invention claimed is:

1. A method for diagnosing and treating non-alcoholic steatohepatitis (NASH) the method comprising:
   (i) measuring levels of blood, serum or plasma circulating hsa-miR-34, YKL-40, and at least one other blood, serum or plasma circulating marker of liver damage of a subject and combining the levels of hsa-miR-34, YKL-40, and the other blood, serum or plasm circulating marker(s) of liver damage through a mathematical algorithm to obtain a NASH score;
   (ii) comparing said NASH score with a threshold value to diagnose moderate and severe NASH or low, moderate, and high NASH activity in the subject; and
   (iii) administering to the subject diagnosed in step (ii) as having severe NASH, low NASH activity, moderate NASH activity, or high NASH activity an effective amount of an anti-NASH compound.

2. The method according to claim 1, wherein said other circulating markers of liver damage are alpha 2 macroglobulin and glycated haemoglobin (HbA1c).

3. The method according to claim 1, wherein said at least one other circulating marker of liver damage is selected from the group consisting of alpha 2 macroglobulin, glycated haemoglobin (HbA1c), fasting glucose level, fructosamine level, insulin, C-Peptide, Homeostasis Model Assessment (HOMA), N-terminal pro-peptide of collagen type III, hsa-miR-200, CK18-M30, CK18-M65, ALT, AST, Uninary Specific Gravity (Uri Spec Grav), uninary creatinine, basophils, High Sensitivity-Reactive Protein (HSCRP), Urinary β-NAG, leucocytes, neutrophils and fibrinogen.

4. The method according to claim 1, wherein the NASH score is calculated according to the following logistic function:

$$S = \frac{e^Y}{1+e^Y}$$

wherein:

$Y = k + a^*A + b^*B + c^*C + d^*D + f^*F + g^*G$ wherein:
S is the NASH score;
A is the level of alpha 2 macroglobulin in g/L;
B is the level of HbA1c in percent;
C is the level of N-terminal pro-peptide of collagen type III in ng/mL;
D is the level of hsa-miR-34a in Cq;
F is the level of hsa-miR-200 or c hsa-miR-200 in Cq;
G is the level of YKL-40 in pg/ml;
k is the constant of the logistic function;
a is a coefficient associated to the level of alpha 2 macroglobulin;
b is a coefficient associated to the level of HbA1c;
c is a coefficient associated to the level of N-terminal pro-peptide of collagen type III;
d is a coefficient associated to the level of hsa-miR-34a or hsa-miR-34a-5p;
f is a coefficient associated to the level of hsa-miR-200, hsa-miR-200a, or hsa-miR-200a-3p; and
g is a coefficient associated to the level of YKL-40;
wherein:
a) the logistic function is derived from a median model, and:
   k is a number between 5.94 and 50.74;
   a is a number between 0 and 1.07;
   b is a number between 0 and 1.20;
   c is a number between 0 and 0.24;
   d is a number between −0.97 and 0;
   f is a number between −0.87 and 0;
   g is a number comprised between 0 and 1.74E-0 a NASH score higher than a threshold value between 0.2017 and 0.4645 being indicative of a severe NASH, or of a moderate or high NASH activity, which is indicative of a patient having a steatosis score ≥1, a hepatocyte ballooning score ≥1, a lobular inflammation score ≥1, a NAS ≥4 and a fibrosis stage ≥2; or
b) the logistic function is derived from a bootstrap model, and:
   k is a number between 8.24 and 35.44;
   a is a number between 0.06 and 0.88;
   b is a number between 0.14 and 1.04;
   c is a number between 0.03 and 0.23;
   d is a number between −0.75 and −0.05;
   f is a number between −0.73 and −0.07; and
   g is a number between 3.59E-06 and 1.78E-05;
   a NASH score higher than a threshold value comprised between 0.2718 and 0.6391 being indicative of a severe NASH, or of a moderate or high NASH activity, which is indicative of a patient having a steatosis score ≥1, a hepatocyte ballooning score ≥1, a lobular inflammation score ≥1, a NAS ≥4 and a fibrosis stage ≥2.

5. The method according to claim 1, wherein the NASH score is calculated according to the following logistic function:

$$S \sim \frac{e^Y}{1+e^Y}$$

wherein: $Y = k + a^*A + b^*B + c^*C + d^*D$;
wherein S is the NASH score;
A is the serum level of hsa-miR-34a in Cq;
B is the serum level of alpha 2 macroglobulin in g/L;
C is the serum level of YKL-40 in pg/ml;
D is the level of HbA1c in percent;
k is a constant of the logistic function;
a is a coefficient associated to the serum level of hsa-miR-34a;
b is a coefficient associated to the serum level of alpha 2 macroglobulin;
c is a coefficient associated to the serum level of YKL-40; and
d is a coefficient associated to the level of HbA1c;

wherein:
a) the logistic function is derived from a bootstrap model, under which:
  k is a number comprised between 9.51 and 34.37;
  a is a number comprised between −1.17 and −0.47;
  b is a number comprised between 0.02 and 0.84;
  c is a number comprised between 6.10E-06 and 2.09E-05;
  d is a number comprised between 0.07 and 0.89;
  a NASH score higher than a threshold value between 0.2013 and 0.5965 being indicative of a severe NASH, or of a moderate or high NASH activity; which is indicative of a patient having a steatosis score ≥1, a hepatocyte ballooning score ≥1, a lobular inflammation score ≥1, a NAS ≥4 and a fibrosis stage ≥2; or
b) the logistic function is derived from the median model, under which:
  k is a number between 6.02 and 56.69;
  a is a number between −1.26 and 0.00;
  b is a number between 0.00 and 0.88;
  c is a number between 0.00 and 2.00E-05;
  d is a number between 0.00 and 0.96;
  a NASH score higher than a threshold value between 0.9773 and 0.9955 being indicative of a severe NASH, or of a moderate or high NASH activity, which is indicative of a patient having a steatosis score ≥1, a hepatocyte ballooning score ≥1, a lobular inflammation score ≥1, a NAS ≥4 and a fibrosis stage ≥2.

6. The method according to claim 5, wherein the logistic function is derived from the bootstrap model, under which:
  k is 21.94;
  a is −0.82;
  b is 0.43;
  c is 1.35E-05;
  d is 0.48; and
  wherein a NASH score higher than a threshold value equal to 0.4661 is indicative of a severe NASH, or of a moderate or high NASH activity, which is indicative of a patient having a steatosis score ≥1, a hepatocyte ballooning score ≥1, a lobular inflammation score ≥1, a NAS ≥4 and a fibrosis stage ≥2.

7. The method according to claim 5, wherein the logistic function is derived from the median model, under which:
  k is 28.17;
  a is −0.84;
  b is 0.36;
  c is 1.23E-05;
  d is 0.41; and
  wherein a NASH score higher than a threshold value comprised between 0.9773 and 0.9955 is indicative of a severe NASH, or of a moderate or high NASH activity, which is indicative of a patient having a steatosis score ≥1, a hepatocyte ballooning score ≥1, a lobular inflammation score ≥1, a NAS ≥4 and a fibrosis stage ≥2.

8. The method according to claim 1, wherein the NASH score is calculated according to the following logistic function:

$$S \sim \frac{e^Y}{1+e^Y}$$

wherein:
$Y = k + a*A + b*B + c*C + d*D$ wherein:
S is the NASH score;
A is the serum level of hsa-miR-34a in copy/µL (log 10);
B is the serum level of alpha 2 macroglobulin in g/L;
C is the serum level of YKL-40 in pg/ml;
D is the level of HbA1c in percent;
k is the constant of the logistic function,
a is a coefficient associated to the serum level of hsa-miR-34a;
b is a coefficient associated to the serum level of alpha 2 macroglobulin;
c is a coefficient associated to the serum level of YKL-40;
d is a coefficient associated to the level of HbA1c;
wherein:
a) the logistic function is derived from a bootstrap model, under which:
  k is a number comprised between −14.50 and −7.40;
  a is a number comprised between 1.38 and 3.58;
  b is a number comprised between 0.02 and 0.84;
  c is a number comprised between 5.98E-06 and 2.08E-05;
  d is a number comprised between 0.07 and 0.89;
  a NASH score higher than a threshold value comprised between 0.1895 and 0.6089 being indicative of a severe NASH, or of a moderate or high NASH activity, which is indicative of a patient having a steatosis score ≥1, a hepatocyte ballooning score ≥1, a lobular inflammation score ≥1, a NAS ≥4 and a fibrosis stage ≥2; or
b) the logistic function is derived from a median model, under which:
  k is a number comprised between −27.16 and −0.78;
  a is a number comprised between 0 and 3.97;
  b is a number comprised between 0 and 0.89;
  c is a number comprised between 0 and 1.98E-05;
  d is a number comprised between 0 and 0.97;
  a NASH score higher than a threshold value comprised between 0.1421 and 0.4556 being indicative of a severe NASH, or of a moderate or high NASH activity, which is indicative of a patient having a steatosis score ≥1, a hepatocyte ballooning score ≥1, a lobular inflammation score ≥1, a NAS ≥4 and a fibrosis stage ≥2.

9. The method according to claim 8, wherein b is 0.38 for the logistic function derived from a median model.

10. The method according to claim 1, wherein the NASH score is calculated according to the following logistic function:

$$S \sim \frac{e^Y}{1+e^Y}$$

wherein:
$Y = k + a*A + b*B + c*C + d*D + f*F;$ wherein:
S is the NASH score;
A is the level of hsa-miR-34a in Cq;
B is the level of YKL-40 in pg/ml;
C is the level of urinary specific gravity with no unit (no units);
D is the level of basophils in 10e9/L;

F is the level of HSCRP in mg/dL:

k is a number between −124.81 and 1.13;

a is a number between −0.91 and −0.25;

b is a number between 4.77e-06 and 2.39e-05;

c is a number between 17.21 and 141.51;

d is a number between 2.80 and 60.74;

f is a number between 0.01 and 0.23; and wherein a NASH score higher than a threshold value between 0.5791 and 0.8269 is indicative of a severe NASH, or of a moderate or high NASH activity, which is indicative of a patient having a steatosis score ≥1, a hepatocyte ballooning score ≥1, a lobular inflammation score ≥1, a NAS ≥4 and a fibrosis stage ≥1.

11. The method according to claim 1, wherein said anti-NASH compound is of formula (I):

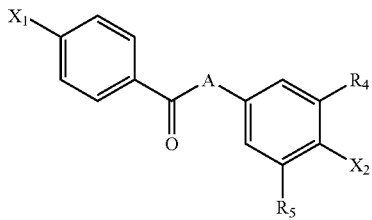

wherein:

X1 represents a halogen, a R1, or G1-R1 group;

A represents a CH=CH or a CH2—CH2 group;

X2 represents a G2-R2 group;

G1 represents an atom of oxygen;

G2 represents an atom of oxygen or sulfur;

R1 represents a hydrogen atom, an unsubstituted alkyl group, an aryl group or an alkyl group that is substituted by one or more halogen atoms, an alkoxy or an alkylthio group, cycloalkyl groups, cycloalkylthio groups or heterocyclic groups;

R2 represents an alkyl group substituted by at least a —COOR3 group, wherein R3 represents a hydrogen atom, or an alkyl group that is substituted or not by one or more halogen atoms, cycloalkyl groups, or heterocyclic groups;

R4 and R5, identical or different, representing an alkyl group that is substituted or not by one or more halogen atoms, cycloalkyl groups, heterocyclic groups;

or a pharmaceutically acceptable salt thereof.

* * * * *